(12) United States Patent
Berger et al.

(10) Patent No.: US 11,207,464 B2
(45) Date of Patent: Dec. 28, 2021

(54) APPARATUS FOR FILLING A SYRINGE WITH A DOSE OF FLUID

(71) Applicant: RESCUE DOSE LTD, Yokneam (IL)

(72) Inventors: Amir Berger, Kiryat Biyalik (IL); Gilad Einy, Haifa (IL); Eli Leshem, Ramat Efal (IL); Boris Rapoport, Haifa (IL)

(73) Assignee: Rescue Dose LTD, Yokneam (IL)

( * ) Notice: Subject to any disclaimer, the term of this patent is extended or adjusted under 35 U.S.C. 154(b) by 0 days.

(21) Appl. No.: 16/973,798

(22) PCT Filed: Jun. 19, 2019

(86) PCT No.: PCT/IB2019/055149
§ 371 (c)(1),
(2) Date: Dec. 10, 2020

(87) PCT Pub. No.: WO2019/244063
PCT Pub. Date: Dec. 26, 2019

(65) Prior Publication Data
US 2021/0121629 A1    Apr. 29, 2021

Related U.S. Application Data

(60) Provisional application No. 62/799,055, filed on Jan. 31, 2019, provisional application No. 62/688,169, filed on Jun. 21, 2018.

(51) Int. Cl.
*A61M 5/178*    (2006.01)
*A61M 5/24*    (2006.01)
(Continued)

(52) U.S. Cl.
CPC ............ *A61M 5/1782* (2013.01); *A61M 5/24* (2013.01); *A61M 5/315* (2013.01);
(Continued)

(58) Field of Classification Search
CPC ...... A61M 5/1782; A61M 5/315; A61M 5/24; A61M 5/3137; A61M 5/3202; A61M 2005/3114; A61M 2005/2488
See application file for complete search history.

(56) References Cited

U.S. PATENT DOCUMENTS 6,364,866 B1 * 4/2002 Furr .................... A61M 5/1782
                                                                141/330
2009/0038709 A1 * 2/2009 VanVreeland ...... B01F 13/1055
                                                                141/18
(Continued)

*Primary Examiner* — Amber R Stiles
(74) *Attorney, Agent, or Firm* — The Law Office of Joseph L. Felber

(57) ABSTRACT

An apparatus for filling a syringe with a verified dose of radiant fluid has a container holder that holds a container of the radiant fluid wherein a syringe oriented at a septum of the container can penetrate the septum. The syringe holder is configured to continuously grip the syringe, to drive the syringe to the container holder and penetrate the septum, to fill the syringe with a dose of the radiant fluid from the container, to drive the syringe to a transfer post, to drive the syringe to a metering zone of a metering station in order to verify that measured radiation is compatible with the dose, and to release the continuous grip.

17 Claims, 17 Drawing Sheets

(51) Int. Cl.
  *A61M 5/31*   (2006.01)
  *A61M 5/315*  (2006.01)
  *A61M 5/32*   (2006.01)

(52) U.S. Cl.
  CPC ........ *A61M 5/3137* (2013.01); *A61M 5/3202* (2013.01); *A61M 2005/2488* (2013.01); *A61M 2005/3114* (2013.01)

(56) References Cited

U.S. PATENT DOCUMENTS

| | | |
|---|---|---|
| 2012/0273087 A1 | 11/2012 | Stavsky et al. |
| 2014/0157731 A1* | 6/2014 | Perazzo .................. B65B 5/045 53/473 |
| 2016/0158105 A1* | 6/2016 | Einy .......................... B65B 3/04 604/414 |
| 2017/0151127 A1 | 6/2017 | Einy et al. |
| 2017/0290993 A1 | 10/2017 | Cowan et al. |

\* cited by examiner

APPARATUS FOR FILLING A SYRINGE WITH A DOSE OF FLUID

TECHNICAL FIELD

Embodiments of the invention relate to an apparatus for filling a syringe with a dose of fluid, for example while continuously gripping the syringe.

BACKGROUND

In medicine, application of substances in diagnosis and/or treatment procedures of a disease or therapeutic procedure is common. One such example may be in Nuclear medicine where substances to be applied to a patient may be radioactive, however other therapeutic procedures may also be applicable. Such substances may be introduced to a patient by Intravenous administration or by any other appropriate means Doses of substances may be prepared for such administration and in some cases doses may be patient specific. Pharmaceutical compounding for example relates to procedures that are taken in order to form tailored medicines or drugs that are suited to address required therapeutic needs of a patient.

Economic and efficient preparation of doses of substances to be administered to a patient is preferable, in particular in cases where many patients require attention such as in a hospital environment (or the like). Nevertheless, it is normally required that doses being prepared be relative accurate in the amounts of substances prescribed for the patient intended to receive same.

SUMMARY OF THE INVENTION

According to an aspect of some embodiments of the invention, there is provided an apparatus for filling a syringe with a verified dose of radiant fluid, comprising: a container holder configured to hold a container of the radiant fluid wherein a syringe oriented at a septum of the container can penetrate the septum; a syringe holder configured to continuously grip the syringe, to drive the syringe to the container holder and penetrate the septum, to fill the syringe with a dose of the radiant fluid from the container, to drive the syringe to a transfer post, to drive the syringe to a metering zone of a metering station in order to verify that measured radiation is compatible with the dose, and to release the continuous grip.

In some embodiments, the syringe holder is further configured to the pull the syringe from the metering zone.

In some embodiments the apparatus further comprising a transport means configured to associate the container holder and the transfer post in order to enable the syringe holder to drive the syringe to the container holder and to the transfer post;

In some embodiments, the transport means is configured to couple the container holder and the transfer post.

In some embodiments, the transport means comprises a linear slide.

In some embodiments, the metering station comprises a dose calibrator.

In some embodiments, the container of the radiant fluid is a vial;

In some embodiments there are more than one container.

In some embodiments, the container holder is associated with an adjustable container shield tray that comprises a shielding member, the shielding member is configured to reduce contamination by radiation whose source is at the radiant fluid in the container.

In some embodiments, the apparatus is configured to adjust the adjustable container shield tray in order to allow a needle coupled to the syringe to access a septum of the container.

In some embodiments, adjust comprises rotating the adjustable container shield tray so as to allow the needle to access the septum.

In some embodiments the shield under the septum hole can be rotate to allow the needle to access the septum.

In some embodiments, the apparatus is further comprising: a cap holder associated with the syringe holder, the cap holder is configured to uncap the needle in order to leave the needle uncovered by gripping the cap while the syringe holder pulls the syringe away from the cap; the cap holder is configured also to recap the needle by gripping the cap while the syringe holder pushes the needle towards the cap holder.

In some embodiments, the apparatus is utilizing vertical separation of components in order to avoid contamination.

In some embodiments, vertical separation is achieved by rotating the syringe holder.

According to an aspect of some embodiments of the invention, there is provided an apparatus for filling a syringe with a dose of fluid, comprising: a container holder configured to hold a container of the fluid, whereby a syringe oriented at a septum of the container can penetrate the septum; a syringe holder configured to: continuously grip the syringe, to drive the syringe to the container holder, to fill the syringe with a dose of the fluid from the container, to drive the syringe to a transfer post, to issue the syringe by releasing the continuous grip.

In some embodiments, the apparatus is further associated with a metering station, configured to verify that the dose is compatible with an expected dose of the fluid;

In some embodiments, the apparatus after the metering station, can continue to grip the syringe and adjust the fluid amount by driving the syringe to the container holder, to thereby adjust the amount of liquid in the syringe and move back to the metering station to verify that the dose was adjusted to the expected dose. This process can be repeated several times.

In some embodiments, the metering station is a camera useable to acquire an image of the syringe, and wherein the apparatus is associated with an image processing device configured to perform the verification based on the image.

In some embodiments, the syringe holder is further configured to drive the syringe to a metering zone of the metering station in order to verify that the dose is compatible with an expected dose of the fluid.

In some embodiments, the syringe holder is further configured to the pull the syringe from the metering zone.

In some embodiments, the apparatus is further comprising a transport means configured to associate the container holder and the transfer post in order to enable the syringe holder to drive the syringe to the container holder and to the transfer post.

In some embodiments the transport means comprises a linear slide.

In some embodiments the container of the fluid is a vial;

In some embodiments, the apparatus further comprising: a cap holder associated with the syringe holder, the cap holder is configured to uncap the needle in order to leave the needle uncovered by gripping the cap while the syringe holder pulls the syringe away from the cap; the cap holder is configured also to recap the needle by gripping the cap while the syringe holder pushes the needle towards the cap holder.

In some embodiments, the apparatus uses vertical separation of components in order to avoid contamination.

In some embodiments, the vertical separation is achieved by rotating the syringe holder.

According to an aspect of some embodiments of the invention, there is provided an apparatus for automatically orienting a needle towards a septum of a container in order to allow the needle to penetrate the septum, the apparatus comprising: a container holder configured to spatially stabilize a septum of a container, to expose the septum to a needle; a first light source configured to reflect a first optical signal that crosses a line perpendicular to a middle of the septum; a first optical sensor configured to receive the first optical signal and to measure an intensity of the first optical signal; and a processor configured to obtain from the first optical sensor an indication relating to the intensity of the first optical signal and upon detecting that the intensity of the first optical signal is maximal, the processor is configured to instruct the syringe holder to spatially adapt the angle of the syringe until the intensity of the received first optical signal reduces.

In some embodiments, the apparatus further comprises a second light source configured to reflect a second optical signal that crosses the line; and a second optical sensor configured to receive the second optical signal and to measure an intensity of the second optical signal; wherein the processor is further configured to obtain from the second optical sensor an indication relating to the intensity of the second optical signal and upon detecting that the intensity of the second optical signal is maximal, and to instruct the syringe holder to spatially adapt the angle of the syringe until the received intensity of the second optical signal reduces.

In some embodiments, the first optical signal is a laser beam.

In some embodiments, the first optical signal is a visible light beam. Other features and advantages of the instant invention will become apparent from the following description of the invention which refers to the accompanying drawings.

Further aspects of the present invention are exemplified in the following:

1. An apparatus for filling a syringe with a verified dose of radiant fluid, comprising: a container holder configured to hold a container of the radiant fluid wherein a syringe oriented at a septum of the container can penetrate the septum; a syringe holder configured to continuously grip the syringe, to drive the syringe to the container holder and penetrate the septum, to fill the syringe with a dose of the radiant fluid from the container, to drive the syringe to a transfer post, to drive the syringe to a metering zone of a metering station in order to verify that measured radiation is compatible with the dose, and to release the continuous grip.

2. The apparatus of aspect 1, wherein the syringe holder is further configured to the pull the syringe from the metering zone.

3. The apparatus of aspect 1, further comprising a transport means configured to associate the container holder and the transfer post in order to enable the syringe holder to drive the syringe to the container holder and to the transfer post.

4. The apparatus of aspect 1, wherein the transport means is configured to couple the container holder and the transfer post.

5. The apparatus of aspect 3 or 4, wherein the transport means comprises a linear slide.

6. The apparatus of any one of aspects 1-5, wherein the metering station is a dose calibrator 7. The apparatus of any one of aspects 1-6, wherein the container of the radiant fluid is a vial.

8. The apparatus of aspect 1, wherein the container holder is associated with an adjustable container shield tray that comprises a shielding member, the shielding member is configured to reduce contamination by radiation whose source is at the radiant fluid in the container.

9. The apparatus of aspect 8, configured to adjust the adjustable container shield tray in order to allow a needle coupled to the syringe to access a septum of the container.

10. The apparatus of aspect 9, wherein adjust comprises rotating the adjustable container shield tray so as to allow the needle to access the septum.

11. The apparatus of any one of aspects 1-10, further comprising: a cap holder associated with the syringe holder, the cap holder is configured to uncap the needle in order to leave the needle uncovered by gripping the cap while the syringe holder pulls the syringe away from the cap; the cap holder is configured also to recap the needle by gripping the cap while the syringe holder pushes the needle towards the cap holder.

12. The apparatus of any one of aspects 1-11, using vertical separation of components in order to avoid contamination.

13. The apparatus of aspect 12 wherein vertical separation is achieved by rotating the syringe holder.

14. An apparatus for automatically orienting a needle towards a septum of a container in order to allow the needle to penetrate the septum, the apparatus comprising: a container holder configured to spatially stabilize a septum of a container, to expose the septum to a needle; a syringe holder configured to spatially stabilize a syringe while the needle coupled to the syringe is oriented towards the septum; a first light source configured to reflect a first optical signal that crosses a line perpendicular to a middle of the septum: a first optical sensor configured to receive the first optical signal and to measure an intensity of the first optical signal; and a processor configured to obtain from the first optical sensor an indication relating to the intensity of the first optical signal and upon detecting that the intensity of the first optical signal is maximal, the processor is configured to instruct the syringe holder to spatially adapt the angle of the syringe until the intensity of the received first optical signal reduces.

15. The apparatus of aspect 14, further comprising: a second light source configured to reflect a second optical signal that crosses the line; a second optical sensor configured to receive the second optical signal and to measure an intensity of the second optical signal; and wherein the processor is further configured to obtain from the second optical sensor an indication relating to the intensity of the second optical signal and upon detecting that the intensity of the second optical signal is maximal, and to instruct the syringe holder to spatially adapt the angle of the syringe until the received intensity of the second optical signal reduces.

16. The apparatus of aspect 14 or 15, wherein the first optical signal is a laser beam.

17. The apparatus of aspect 14 or 15, wherein the first optical signal is a visible light beam.

18. The apparatus of aspect 14 or 15, wherein the first optical signal is an ultraviolet beam.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF THE INVENTION

Figure 1:
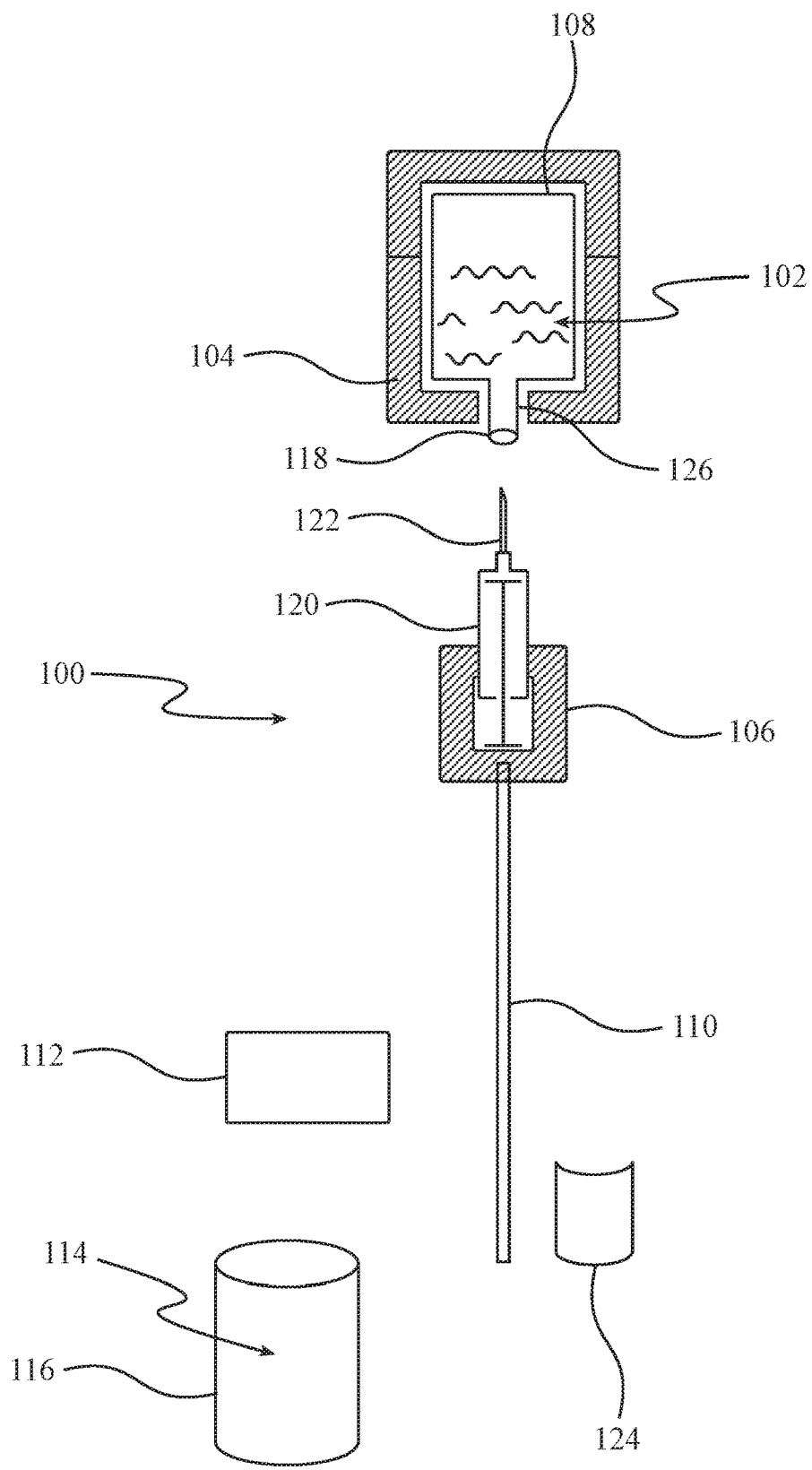
FIG. 1 schematically illustrates an apparatus for filling a syringe with a verified dose of radiant fluid, according to embodiments of the invention.

Before explaining some embodiments of the present invention, it should be appreciated that although various embodiments of the present invention are described herein, these embodiments are only given for the purpose of explaining the present invention, while the present invention should not be considered as being limited to and/or by these embodiments, while it should be appreciated that it would be possible to implement the present invention in various other ways.

In the following description, components that are common to more than one figure will be referenced by the same reference numerals.

In addition, unless specifically noted, embodiments described or referenced in the present description can be additional and/or alternative to any other embodiment described or referenced therein.

FIG. 1 very schematically illustrates an apparatus 100 for filling a syringe with a verified dose of radiant fluid 102, according to at least certain embodiments of the invention. The apparatus here comprises a container holder 104, a syringe holder 106 and a transfer post 112 such as a pig holder where a syringe exiting the apparatus may be held for further use. Container holder 104, syringe holder 106 and transfer post 112 may be associated by a transport means 110.

Container holder 104 in at least certain embodiments may be configured to hold a container 108 of radiant fluid 102—however in other embodiments container holder 104 may be arranged to hold regular non-radiating fluids. When containing a radiant fluid 102 container 108 may radiate, and thus container holder 104 may preferably be a substantially closed container. In medicine, for example, the radiant fluid may be used for nuclear medicine. However, this is non-limiting and radiant fluids are applicable in other fields as well, such as for scientific, agricultural or industrial purposes, etc.

It is possible to manufacture container holder 104 from materials comprising radiation-opaque materials, such as Tungsten, thereby preventing, or at least lowering, contamination of the container holder's environment by radiation. In order to fill a syringe 120 with radiant material 102, according to embodiments of the invention, a needle 122 coupled to the syringe may be arranged to penetrate a septum 118 of container 108, therefore container holder 104 may preferably be provided with an opening ("septum opening" 126) allowing needle 122 to access septum 118. Septum opening 126 may permit some radiation to seep out of the container and contaminate the environment outside container holder 104 and therefore a solution is proposed by embodiments of the invention (see FIG. 3A, FIG. 3B and FIG. 3C below) to mitigate such contamination. Furthermore, container holder 104 may be configured to spatially stabilize the septum 118 of container 108, thereby exposing the septum to the needle and allowing the needle to penetrate therethrough. The needle should better be perpendicular to the septum while deviation of a few degrees from perpendicular can be acceptable.

Transport means 110 may be configured to enable syringe holder 106 to drive the syringe 120 between the container holder 104 and transfer post 112 and vice versa. Transport means 110 may comprise, e.g., a linear slide (see FIG. 2) serving as a guide for a motorized syringe holder 106.

Figure 2:
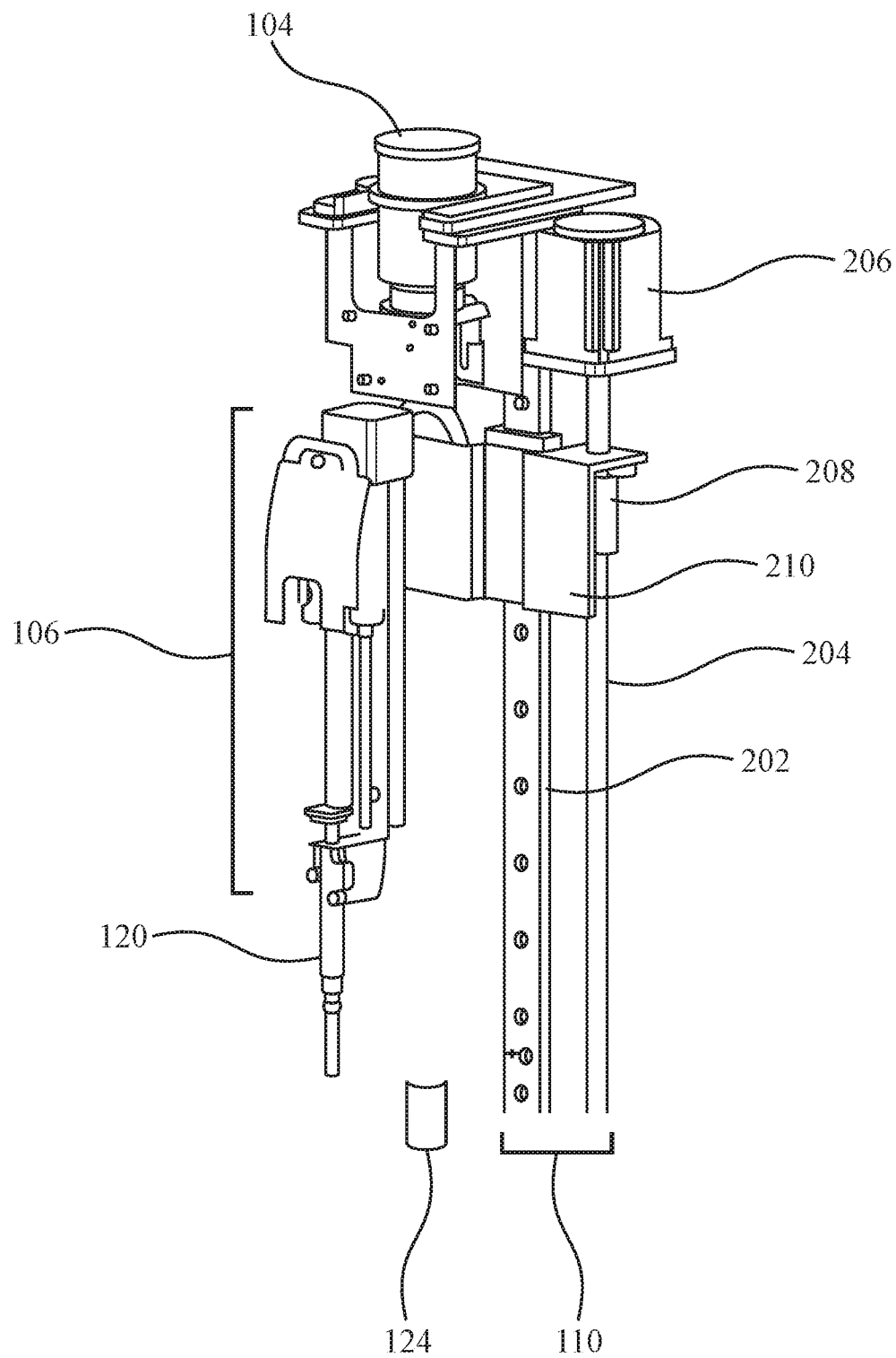
FIG. 2 illustrates the apparatus of FIG. 1 in more details, according to embodiments of the invention.

FIG. 2 illustrates the apparatus of FIG. 1 in more detail, according to embodiments of the invention. As shown in the figure, transport means 110 comprise a linear slide 202 and here a possible lead screw 204. A motor 206, which in the illustrated embodiments may be a linear actuator motor, rotates the linear screw 204 in order to induce motion. A linear nut 208, coupled to a transport element 210, transforms the rotation of the lead screw and allows transport element 210 to ascend and descend along linear slide 202, which provides transport element 210 with stability.

Transport element 210, in turn, may be coupled to syringe holder 106, thereby enabling its ascent and descent. Hence, syringe holder 106 in this optional example may be seen associated with transport means 110 via transport element 210. It is noted that while above, certain details have been provided for exemplifying movement within transport means 110, other suitable solutions may also be used for achieving required movements of the syringe holder 106 within the apparatus.

Because in the illustrated embodiments container 108 stores radiant fluid 102, it may be desired to reduce the probability of contamination of syringe 120 by radiant fluid that may leak through septum 118 and/or opening 126. In addition, it may also be desired to reduce the probability that the apparatus and/or components the apparatus comprises, and/or an environment of the apparatus may be contaminated by leaking fluid. Therefore, in the illustration, transfer post 112 may not necessarily be positioned directly below container holder 104, but rather on the side. That is, the apparatus illustrated in FIG. 1 uses vertical separation of components in order to avoid contamination.

Moreover, it may be possible to place a protective collector, such as a tungsten container, below the septum, i.e., in the same vertical plane of the septum, to collect leaking fluid instead of letting it spread in the apparatus' close environment. Such a collective collector 124 is illustrated both in FIG. 1 and in FIG. 2, though it is noted that this form and position of protective collector 124 is non-limiting.

Having said that, it can be understood that vertical separation and protective collector 124 could also protect a technician accessing the environment of apparatus 100, e.g., for loading a new syringe onto syringe holder 106 at a loading state of the apparatus (see loading state discussed with reference to FIG. 8 onwards) or for any other task.

It can be appreciated that it may be beneficial to verify that the dose of radiant material in the syringe is indeed as expected. Those versed in the art would appreciate that it is possible to measure radiation of the radiant material in the syringe (constituting "measured radiation"). In addition, knowing the volume of the radiant material in the syringe (i.e., the "dose") and the characteristics of the radiant material, it is possible to calculate the expected radiation from the radiant material in the syringe ("expected radiation"). Hence it is possible to compare the measured radiation with the expected radiation thus verifying that the measured radiation is compatible with the dose.

In order to measure radiation and verify that it is indeed compatible with the dose a metering station 116 that is illustrated in FIG. 1 can be associated with or included within the apparatus. For radiant fluids dose calibrators can be used, such as Capintec's® dose calibrators. It is noted that similar to transfer post 112, in some embodiments metering station 116 as well may not be positioned directly below container holder 104, i.e., in the same vertical plane, thereby preventing contamination by leaking radiant fluids. That is, vertical separation may be used herein as well. Furthermore, because radiant fluid 102 in container 108 may be a source of radiation ("source radiation"), in certain embodiments vertical separation of metering station 116 and container holder 104 may assist in maintaining the reading in metering station 116 accurate while avoiding contamination of the reading by source radiation.

At least certain metering stations 116, such as Capintec's® dose calibrators, may be provided with an internal space into which a syringe to be verified may be placed for reading/sensing the liquid dose within the syringe. Such space may be referred to as metering zone 114. While Capintec's® dose calibrators are non-limiting metering station embodiments 116 may be provided with metering zones 114 which may not necessarily be formed as internal spaces.

For example, if the dose calibrator is an external unit metering radiation of syringes positioned in the front thereof, then the zone in front of this external unit, where the syringe can be positioned for reading, may form a metering zone 114. Moreover, this is applicable also for metering stations which meter other characteristics which are not necessarily only radiation. For example, a camera may be considered a metering station 116 if image processing of images taken thereby are used, e.g., for verification of the volume of the fluid within the syringe. In such a case, the camera forms a metering station 116, while the metering zone 114 is the space in front of the camera where the syringe needs to be positioned in order to acquire an image thereof, to be used by the image processing.

Additionally or alternatively, more than one metering station 116 can be used. For example, the syringe may be placed in the metering zone 114 of a metering station 116 which is a camera, and thereafter it can be placed in a metering zone 114 of a metering station 116 which is a dose calibrator, such as the internal space of the dose calibrator.

Returning to FIG. 1, e.g. prior to reaching transfer post 112 the syringe holder can either drive the syringe to a metering zone 114 of a metering station 116, or it can release the syringe e.g., at said transfer post or pig holder for further handling. Such transfer post or pig holder (seen e.g. in FIG. 8 onwards) may be lead shielded for accommodating unshielded syringes. Otherwise, a released syringe can be disposed, for example if verification fails.

Figure 3A:
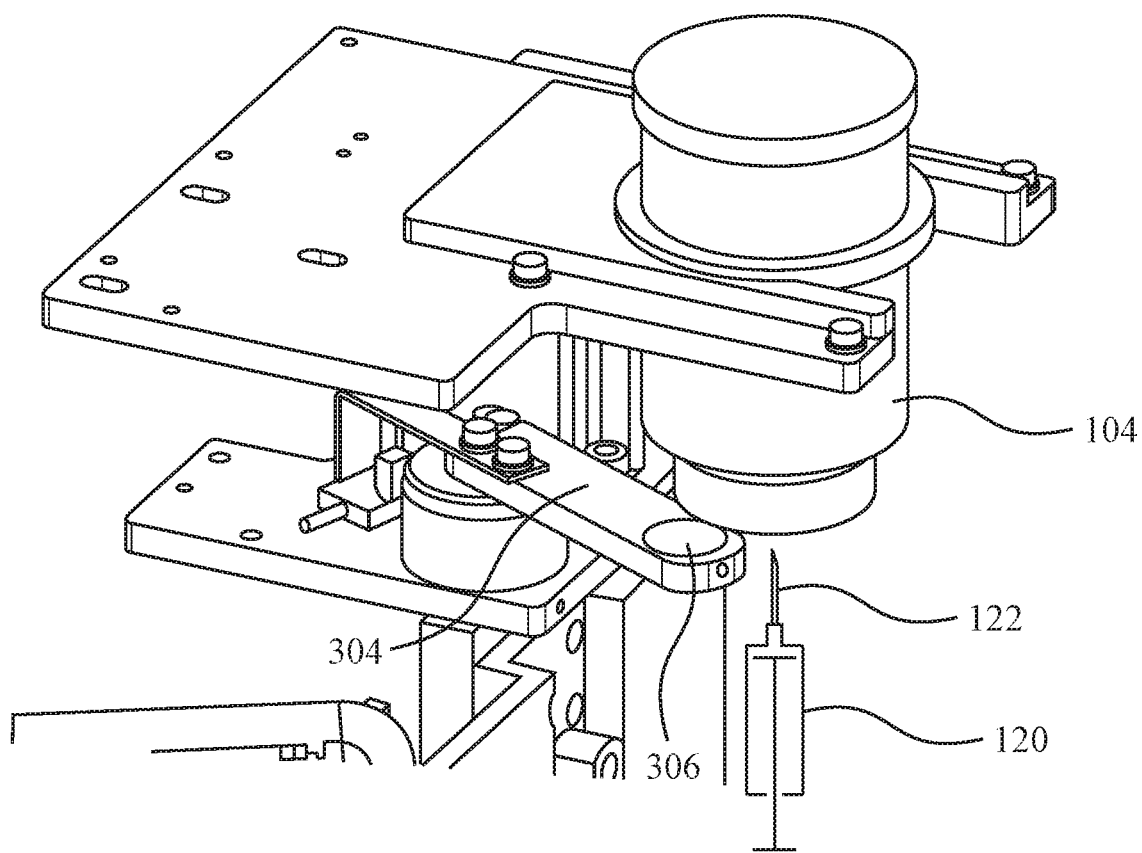
FIGS. 3A to 3C illustrate a mechanism of the apparatus for substantial prevention of contamination, according to embodiments of the invention.
Figure 3B:
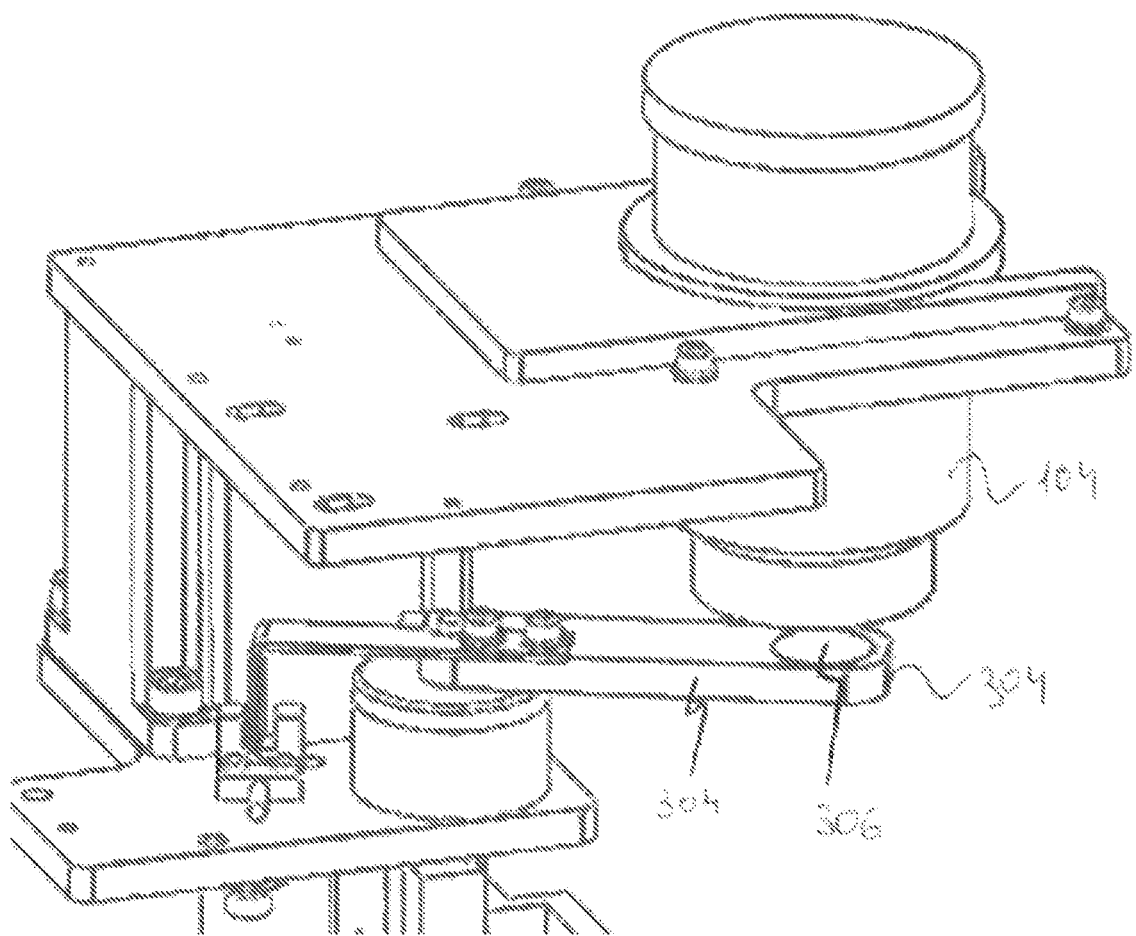
Figure 3C:
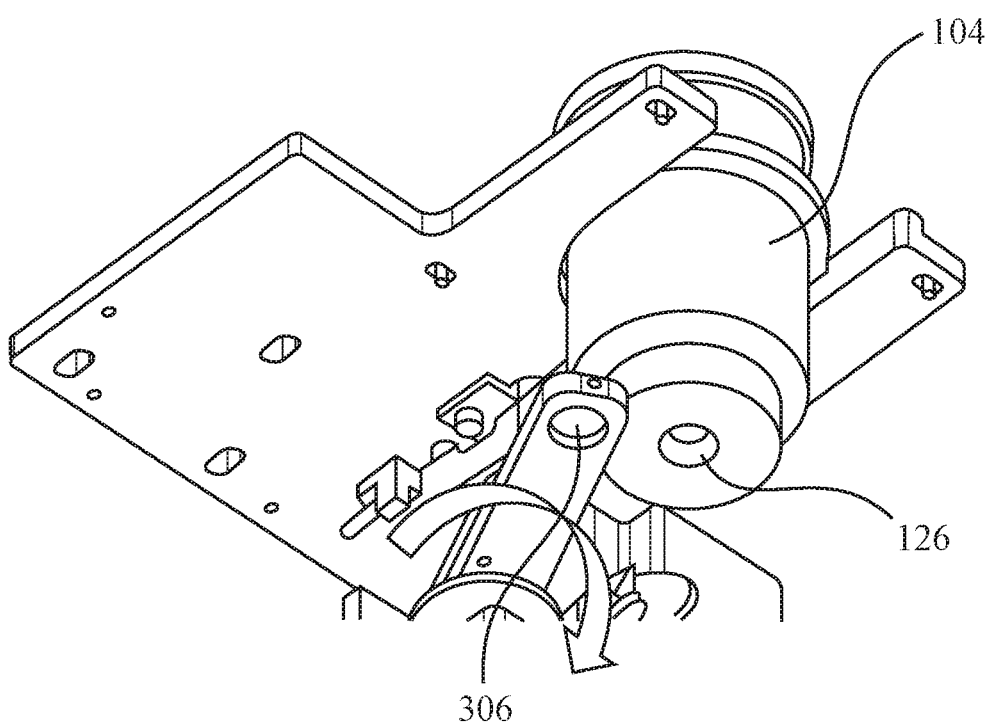

It was mentioned before, with reference to FIG. 1, that radiation may leak through septum opening 126, contaminating the environment around container holder 104, including contamination of the reading in metering station 116. FIG. 3A, FIG. 3B and FIG. 3C illustrate a mechanism for preventing contamination, according to at least certain embodiments of the invention. It was previously explained that container holder 104 may be configured to hold a container 108 that stores radiant fluid. FIG. 3C illustrates container holder 104 from below, wherein septum opening 126 can be seen.

In order to prevent contamination by radiation, embodiments of the invention may be arranged to utilize a shielding member 306, e.g. made of tungsten, that may be configured to conceal and substantially close septum opening 126, thereby substantially preventing or reducing contamination. In at least certain embodiments, such "closing" of the septum cannot be permanent, as opening of the septum may at least momentarily be facilitated in order to permit needle 122 to penetrate the septum.

Therefore, at least certain embodiments of the invention may disclose an adjustable container shield tray 304, that may be configured to bring the shielding member 306 towards the septum opening, and later on, to remove the shielding member, thereby allowing needle 122, that is coupled to syringe 120, to access septum 118 of container 108. In the embodiments presented by FIGS. 3A and 3B the adjustable container shield tray 304 is illustrated. In FIG. 3B adjustable container shield tray 304 is beneath septum opening 126, while in FIG. 3A adjustable container shield tray 304 is adjusted to allow needle 122, coupled to syringe 120, to access septum opening 126 and therefore septum 118 of container 108.

According to some embodiments, adjustable container shield tray 304 may be made of radiation shielding materials such as tungsten and shielding member 306 may be part of adjustable container shield tray 304, unlike being a distinct member, coupled to the adjustable container shield tray 304. However, since shielding materials such tungsten may be expensive, heavy metal and reducing cost and weight may be beneficial. Therefore, according to at least certain embodiments of the invention, realizing that it is only the shielding member 306 that obstructs radiation, it may be appreciated that while shielding member 306 should be made of such shielding materials, remainder portions of the adjustable container shield tray 304 can be made of other materials, which are cheaper. Moreover, intermediates are allowed as well. Hence, in some embodiments, a tungsten part larger than the shielding member 306 may exist, while the rest of adjustable container shield tray 304 can be made of cheaper materials.

It should be appreciated that in a laboratory environment where embodiments of the apparatus may be used, where syringes are filled with radiant fluid, preparation time may be a significant consideration. For example, if filling a syringe with a dose of radiant fluid requires approximately 20 seconds (for example), from loading an empty syringe onto the apparatus and until the filled syringe reaches the transfer post or pig holder (even without verification), this means that the apparatus may fill up to 180 syringes an hour. However, if filling a syringe requires, e.g., 120 seconds, no more than 30 syringes can be filled.

Therefore, it can be beneficial to accelerate the process of filling the syringe. Understanding this, it can be appreciated that unloading and loading a syringe to the syringe holder is time consuming and reducing the number of such unloads/loads is thus beneficial. Accordingly, in the disclosed embodiments the syringe holder is configured to substantially continuously grip a syringe. Upon loading a syringe to the syringe holder, the holder grips the syringe and preferably does not release it prior to filling the syringe, or possibly even after verification that measured radiation is compatible with the dose of the radiant fluid filled into the syringe.

Figure 4A:
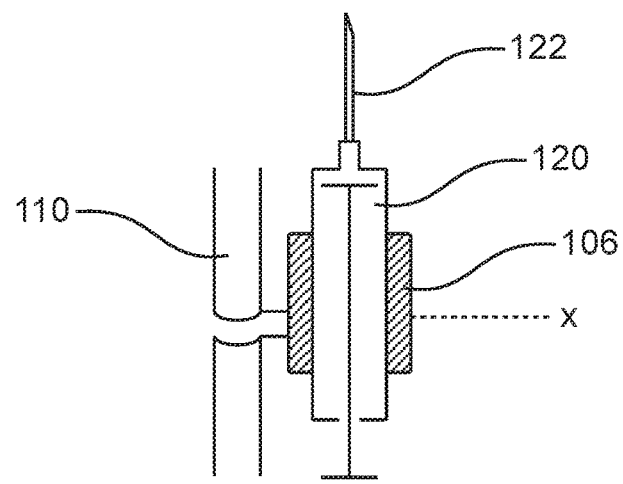
FIGS. 4A to 4C illustrate possible manipulations made by an embodiment of a syringe holder of the apparatus that is arranged to move a syringe held within the apparatus between various positions.
Figure 4B:
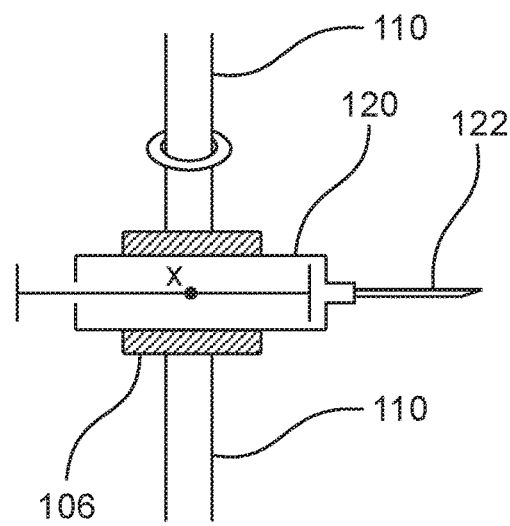
Figure 4C:
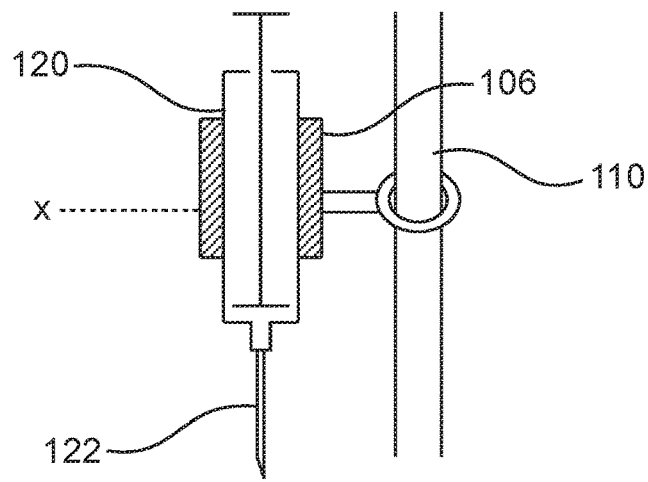

Having understood that the syringe holder may be configured to continuously grip the syringe, and remembering that vertical separation may be beneficial for preventing contamination, attention is drawn now to FIG. 4A, FIG. 4B and FIG. 4C, illustrating rotation of the syringe holder in order to achieve vertical separation without releasing the grip, according to at least certain embodiments of the invention.

It can be seen that the syringe in FIG. 4A, which is positioned facing upwards with its needle oriented up, is in a different vertical plane, compared to the syringe in FIG. 4C, which is positioned with the needle oriented downwards. The syringe in FIG. 4B may illustrate transition between FIGS. 4A and 4C possibly including rotational transition that may be applied to the syringe while being manipulated within the apparatus. Such rotation may be applied about an axis X via a possible hub of the apparatus that may be coupled to transport means 110 (see hub further specified with respect to FIG. 8 onwards). Transport means 110 in turn may be used for urging movements along a vertical axis generally perpendicular to axis X.

Returning now to the container holder 104. As e.g. described with reference to FIG. 1, needle 122 penetrating septum 118 has a small penetration plane or zone through which it should preferably penetrate in order to reach fluid 102 within the container. It should be appreciated that a small deviation of the needle's angle from a line generally perpendicular to the septum may result in missing the septum.

Thus, the apparatus via, inter alia, the syringe holder should optimally drive the syringe towards the septum with the needle substantially perpendicular thereto. However, this may not always be the case, e.g. due to a faulty needle, due to displacement of the syringe within the syringe holder, and/or due to any other reason. Deviations of such needle from the line perpendicular to the septum may result in missing the septum and/or meeting the septum near its borders, where penetration successful cannot occur.

Figure 5:
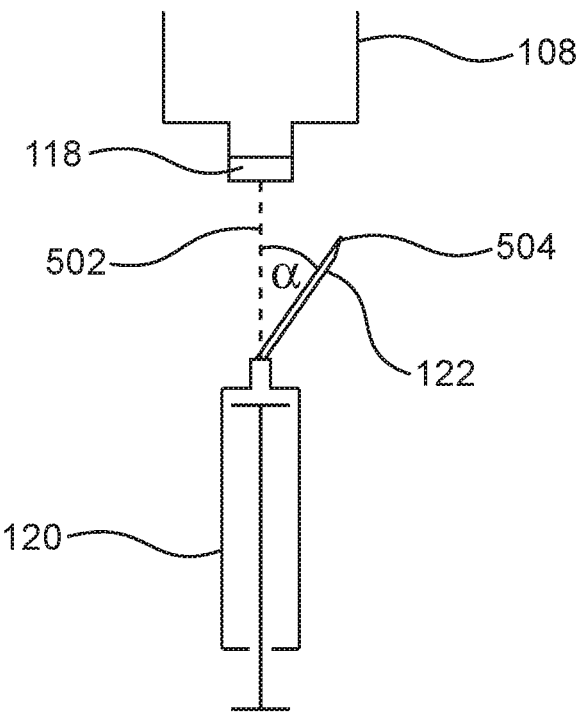
FIG. 5 schematically illustrates a faulty here bent needle approaching a septum, according to embodiments of the invention.

This is schematically illustrated in FIG. 5, wherein a syringe 120 is driven towards septum 118 of container 108. However, the illustrated needle 122 may here be faulty, deviating by angle α from imaginary line 502, which is perpendicular to a face of septum 118. It can be seen in the figure that the tip of the needle, in this case, may miss septum 118, and consequently not penetrate it. In such cases the syringe and needle may be declared useless. However, according to at least certain embodiments of the invention, a mechanism may be suggested for correcting (preferably automatically) such faults and thereby utilizing such "faulty" syringe and/or needle.

Prior to advancing further with the description, it is noted that in FIG. 5 the deviation angle α is wide angle while in reality syringes or needles with such a wide angle of deviation would probably be rejected in advance (possibly via manual inspection), before reaching the apparatus, the syringe holder and the septum. Thus, "faulty" syringes/needles with narrower angles of deviation (α) may be suggested to be used, wherein the deviation is not as clear to the human eye as in the figure. However, in the figure and in further figures as well, such wide angle α may be illustrated in order to clearly demonstrate the essence of the problem and the solutions therefor.

Figure 6:
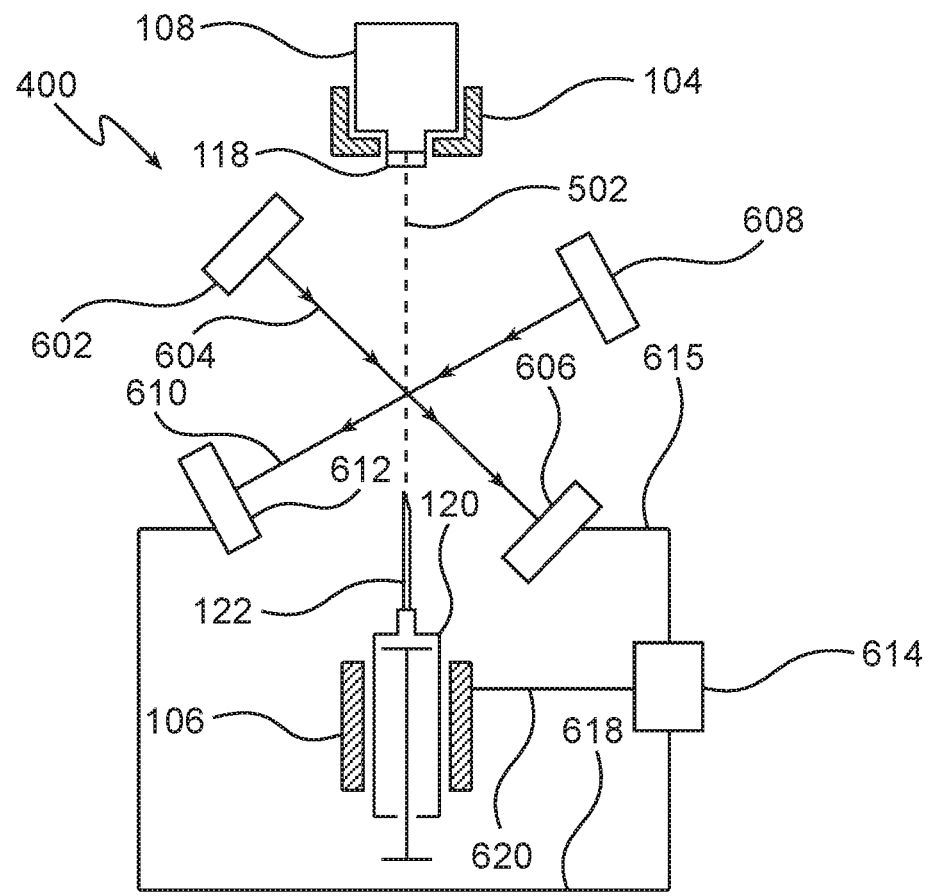
FIG. 6 illustrates an apparatus for automatically orienting a needle towards a septum of a container, according to embodiments of the invention.

FIG. 6 illustrates an embodiment of an optional calibration apparatus 400 for automatically orienting a needle towards a septum of a container in order to allow the needle to penetrate the septum, according to embodiments of the invention. A container holder 104 is illustrated while spatially stabilizing a septum 118 of a container 108, thereby exposing septum 118 to a needle 122. Line 502 is an imaginary line perpendicular to the center of the septum and in a proper condition (as illustrated in the figure) needle 122 may be substantially aligned with the perpendicular line 502.

An embodiment of a syringe holder 106 is also depicted, wherein the syringe holder is configured to spatially stabilize a syringe 120 while needle 122 that is coupled to syringe 120 is oriented here upwards towards septum 118. An embodiment of mechanism for aligning between needles and septum may include optical means. Here, a first light source 602 may be configured to reflect a first optical signal 604 that crosses imaginary line 502, which is substantially perpendicular to the center of septum 118.

Also illustrated is a first optical sensor 606 that is configured to receive first optical signal 604 and to measure its intensity. In a proper condition, needle 122 is expected to cross first optical signal 604 and therefore to reduce the intensity of the first optical signal received by the first optical sensor 606. However, if the needle 122 is not aligned with imaginary line 502, as was previously explained with reference to FIG. 5, it may not cross the first optical signal 604 and therefore first optical sensor 606 will receive the full, maximal intensity of first optical signal 604.

Those versed in the art would understand that there is a very low probability that a non-aligned needle would still cross the first optical signal. This low probability can be substantially reduced by adding further optical sensors, such as here a second light source 608, which reflects a second optical signal 610 that crosses imaginary line 502, and a second optical sensor 612 that is configured to receive second optical signal 610 and to measure its intensity. If needle 122 is aligned with imaginary line 502, the intensity received by both sensors 606 and 612 may be reduced. If only one sensor receives a reduced intensity optical signal this means that the other optical signal is not disturbed by the needle and therefore the needle cannot be aligned.

It is noted that in the embodiments, first optical signal 604 and/or second optical signal 610 can be horizontal or sloped.

The figure depicts also a processor 614, that is associated with sensors 606 and 612, and with syringe holder 106. Association, in this case can be a wired association wherein there are wires, each wire may be physically connected to processor 614 and to one or more of the two sensors (606, 612) and/or to syringe holder 106. Alternatively, the association can be wireless, e.g., using wi-fi, Bluetooth or any other wireless communication protocol proper to the case. A combination may be suitable as well, wherein one or more of the associations may be wired and the other one or more associations may be wireless. In the figure the three associations are symbolically depicted and numbered 616, 618 and 620.

Figure 7A:
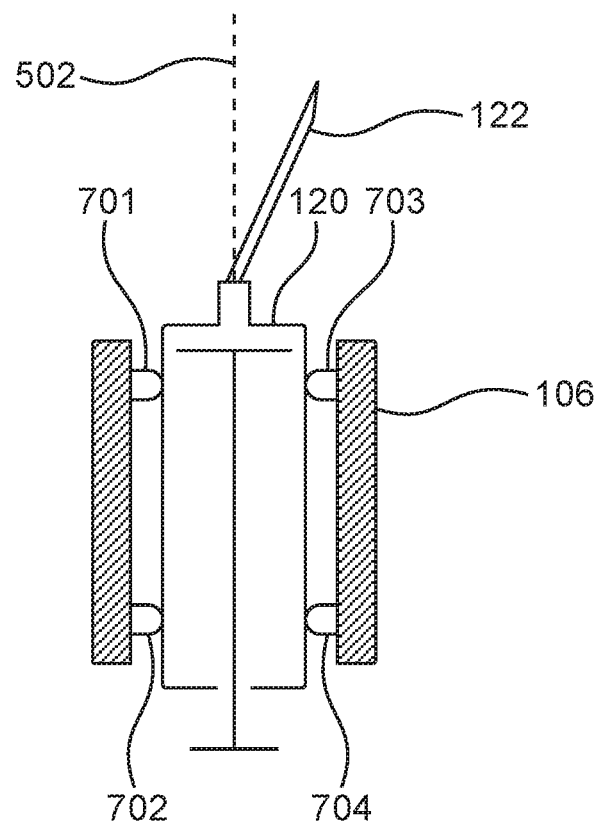
FIGS. 7A and 7B illustrate an exemplary apparatus for aligning a needle, according to embodiments of the invention.
Figure 7B:
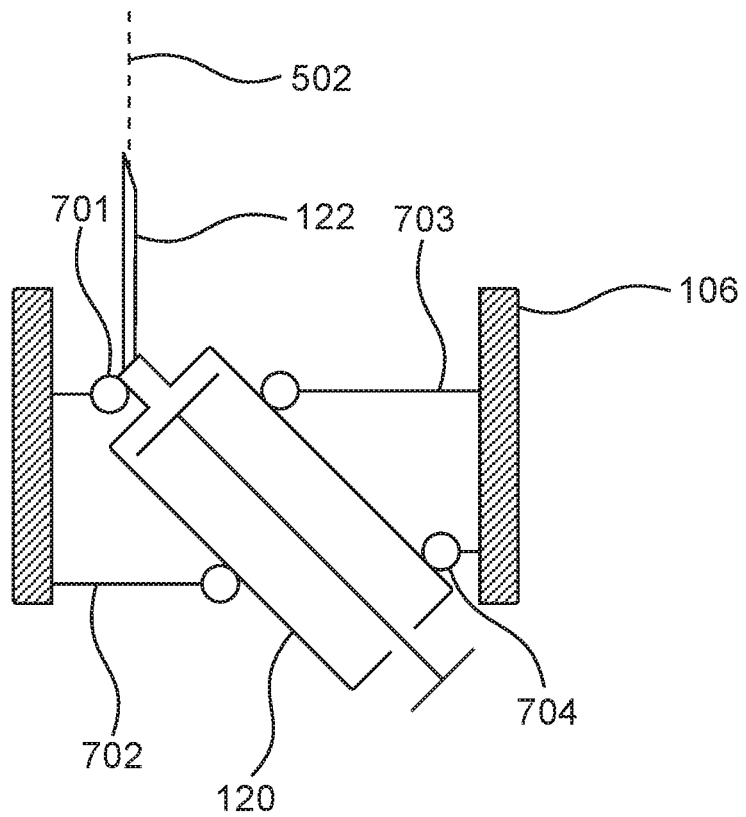

Processor 614 obtains intensity indications from sensors 606 and 612 (or only from one of them in embodiments wherein only one optical signal is used) and responsively controls syringe holder. In order to understand an optional manner how the syringe holder can be controlled, FIG. 7A and FIG. 7B are provided. In FIG. 7A a syringe holder 106 is schematically depicted, holding a syringe that is not aligned with imaginary line 502. In addition, there are four spatial stabilizers depicted, namely these are first stabilizer 701, second stabilizer 702, third stabilizer 703 and fourth stabilizer 704. The four stabilizers may be, for example, springs, which grip syringe 120 and spatially stabilize it to prevent it from moving freely within syringe controller 106.

If needle 122 needs to be aligned, processor 614 (unseen in FIG. 7A and FIG. 7B) controls the stabilizers so as to change the angle of syringe 120 within syringe holder 106, until the optical sensors 606 and 610, or a single sensor (either 606 or 610) if only one optical signal is utilized, indicate that needle 122 is aligned. That is, the angle of syringe 120 is adapted until the intensity received of the first optical signal and/or the second optical signal reduces.

The apparatuses presented with reference to FIG. 6, FIG. 7A and FIG. 7B can be combined with the apparatus of FIG. 1.

In the embodiments presented above, with reference to FIG. 5 and FIG. 6, it can be appreciated that in some cases relative high accuracy may be obtained as sensors 606 and 612 are required to detect very fine modifications in the signal intensities. In addition, needle 122 may be expected to be substantially in the center, where the two signals (604, 610) cross each other.

At least certain embodiment of the invention present, therefore, alternative embodiments that are easier to implement and allow for less accuracy. According to these embodiments, an optical signal may be positioned in front of the container holder's wall adjacent to where septum opening 126 is formed. The optical signal, i.e., a light source and a sensor, may be placed in a way that a needle of a rotating syringe (see FIG. 4A, FIG. 4B and FIG. 4C) would necessarily cross the signal prior to reaching its position in front of the septum opening. The signal may neither required to be perpendicular to the container holder's wall, nor it is required to cross the imaginary line perpendicular to the center of the septum (see, e.g., imaginary line 502 in FIG. 5).

In a possible calibration phase, utilizing an ideal syringe (or a substitute thereof) in which the deviation angle α (see FIG. 5) is zero or near zero, the syringe holder may be verified to hold the ideal syringe (or substituting "calibration device") straight and the position of the syringe holder providing an alignment with imaginary line 502 may be determined (constituting "ideal alignment position"). Thereafter, the syringe holder may be allowed to rotate while holding the ideal syringe (or calibration device), the crossing of the optical signal may be detected, and the angular distance from the crossing of the optical signal to the ideal alignment position may be determined. It is noted that the angular distance can be expressed in terms of angle or in motor steps or in any other term applicable to the case.

After such possible calibration is done, when the apparatus is operational, it can be appreciated that after needle 122 crosses the optical signal, rotating an additional angular distance will bring it to an aligned position.

Further to understanding how a needle is aligned to penetrate septum 118 of container 108, it should be appreciated that after filling the syringe with a dose of the radiant fluid from the container, syringe holder 106 may drive the syringe towards transfer post 112.

Prior to further driving the syringe to metering station 116, it may be required to place a cap over needle 122, in order to assure that metering station 116 is not contaminated by radiant fluid leaking through the needle. Therefore, a cup holder may be disclosed (see further specified in FIG. 8 onwards). The cap holder may be configured to uncap the needle in order to leave the needle uncovered by gripping the cap while the syringe holder pulls the syringe away from the cap; the cap holder may be configured also to recap the needle by gripping the cap while the syringe holder pushes the needle towards the cap holder.

A needle cap is an elongated narrow structure and reverting to the explanation of the importance of aligning a needle while penetrating a septum (see FIG. 5) it can be appreciated that aligning the needle with an imaginary line perpendicular to the center of the cap cross-section is even more critical, as the cap cross section is normally smaller than the cross section of a septum. In addition, the depth of a septum is much shorter than the depth of a needle cap. Therefore, a deviation angle α that may be generally negligible in a septum may turn out to be critical in the case of a needle cap.

Accordingly, in some embodiments, it is possible to place an optical signal in front of the cap opening, calibrate the apparatus and perform a process similar to the one performed in front of the septum. However, if the ideal alignment position had been determined with reference to the septum, and after needle 122 crossed the optical signal there, it may be possible to save the additional installation.

Reverting to the signal crossing at the septum, it may be appreciated that if a specific needle 122 has a deviation angle α that is non-zero, it will cross the optical signal before or after an ideal needle (such as the calibration device) would. Consequently, by rotating an additional angular distance, the needle would be aligned indeed, though the position of the syringe holder (constituting "needle specific alignment position") would not be identical to the ideal alignment position.

In order to align the needle with the cap holder, in at least certain embodiments it may be possible to calculate a "correction value" that may be defined by the difference between the needle specific alignment position and the ideal alignment position ("alignment deviation") with reference to the septum. Thereafter, when the same syringe and needle arrive at the transfer post and alignment between the needle and cap is required, the aforementioned "correction value" may be used to suitably align the needle to the cap.

Therefore, by calibrating the apparatus with reference to the cap holder, determining thereby the "cap ideal alignment position" e.g. around axis X, and reducing the alignment deviation therefrom, it may be possible to substantially determine the needle specific alignment position with reference to the cap in this example about axis X. Hence, it is possible to place the cap onto the needle, further driving the syringe to the metering zone of the metering station in order to verify that measured radiation is compatible with the dose.

Figure 8:
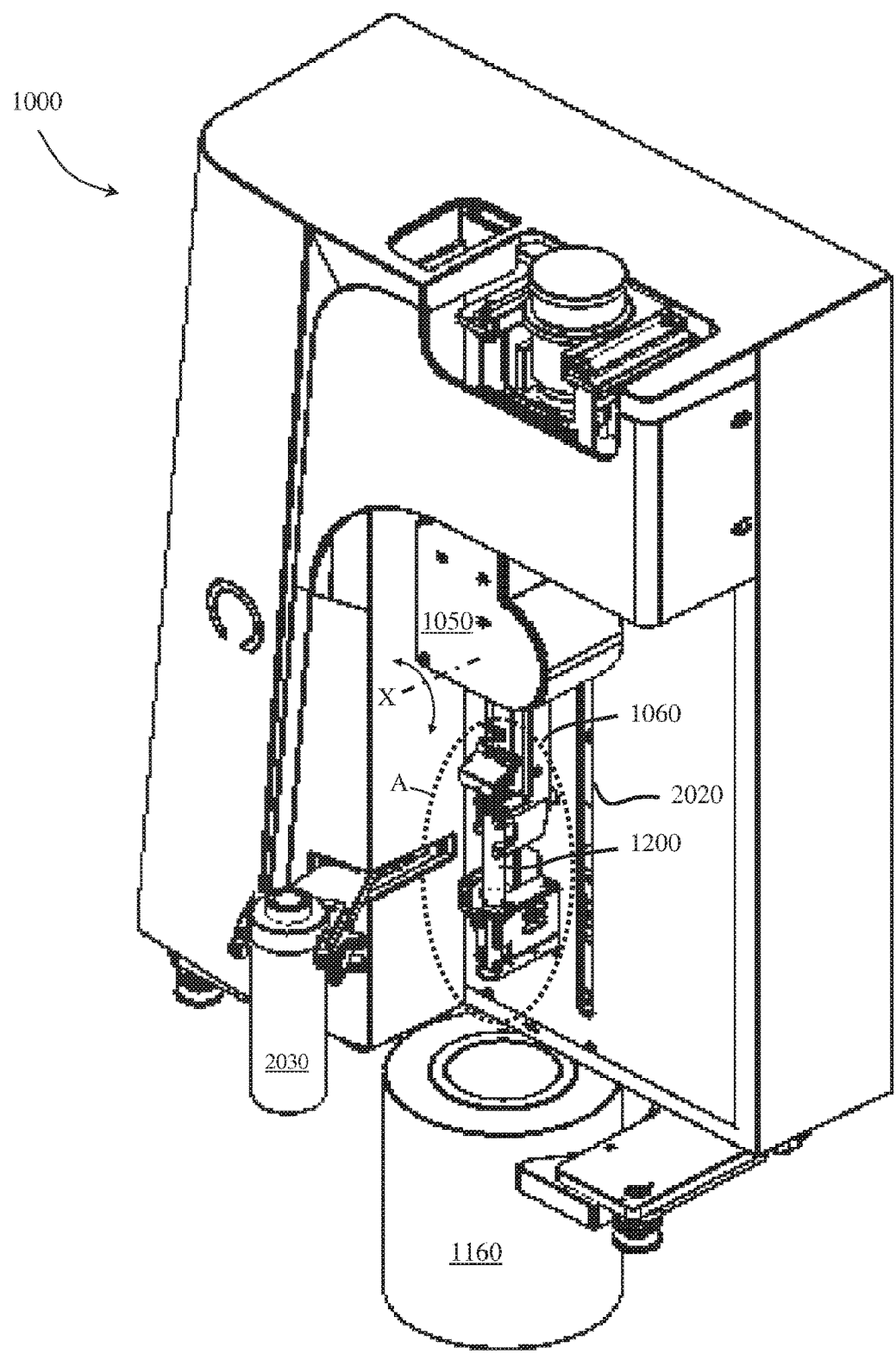
FIGS. 8 to 15 illustrate an embodiment of an apparatus for filling a syringe with a verified dose of radiant fluid during various stages or states of operation.

Attention is now further drawn to FIG. 8 schematically illustrating an embodiment of an apparatus 1000 for filling a syringe 1200 with a verified dose of radiant fluid. Apparatus 1000 in this example (as in at least most embodiments herein) is seen including a transport means and/or slide 2020, a hub 1050 and a syringe holder 1060 that extends/projects away from the hub (see dashed arrow in FIG. 10 exemplifying holder portions exposed beyond the hub) and is arranged to hold a syringe 1200 while being manipulated within the apparatus. Syringe holder 1060 may be coupled to hub 1050, which in turn may be arranged to move both linearly along the slide and rotationally about an axis X generally perpendicular to the slide. Apparatus 1000 is here further seen including a metering station 1160 and a transfer post or pig holder 2030.

Figure 9B:
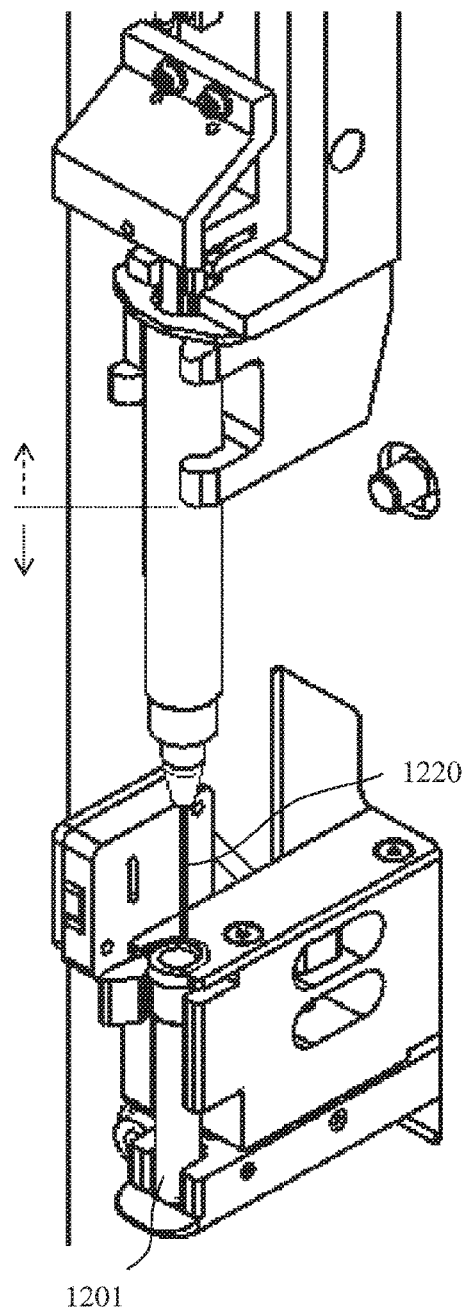
Figure 9A:
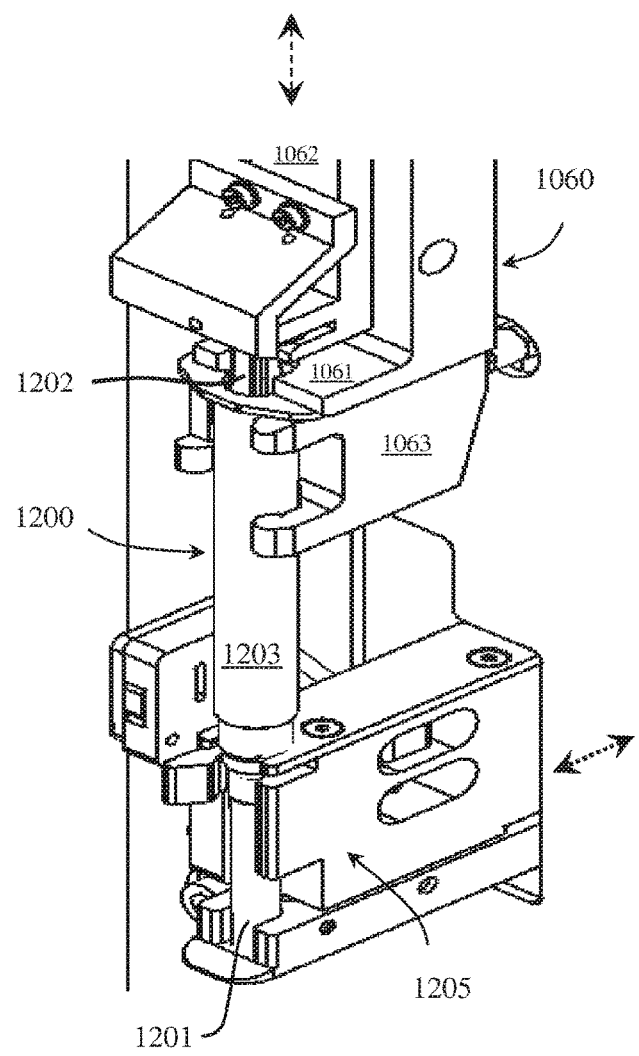

Attention is additionally drawn to FIGS. 9A and 9B for a better view of section A indicated by the dashed ellipse in FIG. 8. FIG. 9A represents a possible loading state of the apparatus in which a syringe may be loaded (possible manually) onto the apparatus. The view of FIG. 9A may be taken to illustrate the apparatus immediately after loading a syringe 1200 thereto. The syringe 1200 here includes a cap 1201 that covers a needle 1220 located at a forward end of the syringe (see needle visible in FIG. 9B). The syringe in addition typically includes a plunger 1202 with a flange located at its rear end.

The apparatus at its loading state is seen including a cap holder 1205: and the loading of a syringe onto the apparatus may include snapping the syringe into position on the apparatus—here by snapping cap 1201 into the cap holder 1205 and a barrel 1203 of the syringe into a snap 1063 of the syringe holder 1060. Syringe holder 1060 may in addition include a bracket 1061 located above snap 1063 and a sway member 1062—and the snap fitting of the syringe onto the apparatus may include urging the barrel's flange in between the bracket and the snap and the plunger's flange into engagement with sway member 1062.

Figure 10:
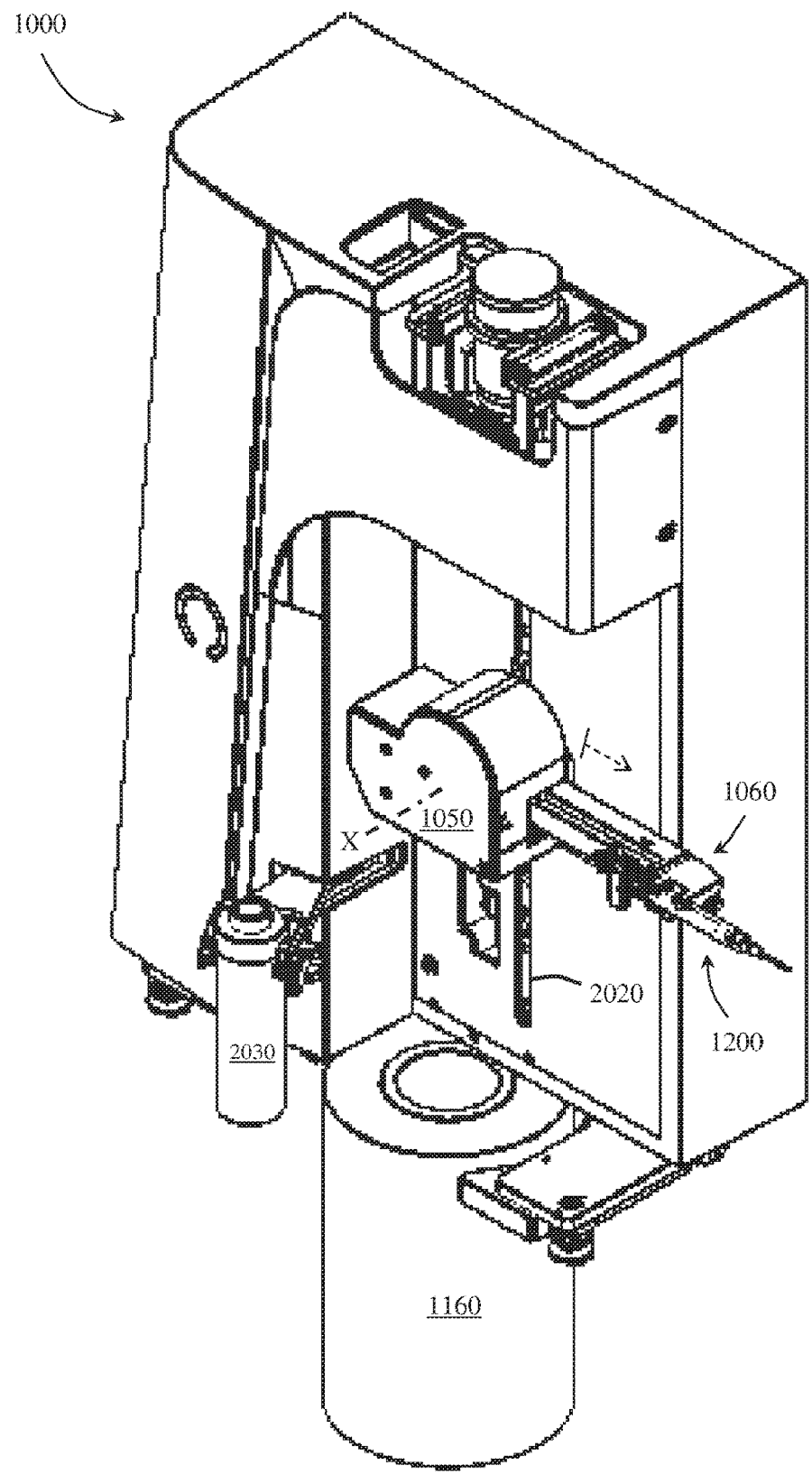

In preferred embodiments—parts of the apparatus—in particular parts of the syringe holder extending away from the hub (e.g. bracket 1061, snap 1063, sway member 1062 and/or syringe holder portions exposed beyond the hub—see dashed arrow in FIG. 10)—which are adapted to enter and/or reach proximity of the metering station—may be chosen to be made substantially from plastic materials that substantially less interfere with measurements made at the metering station. In certain embodiments, substantial formation of the syringe holder from plastic materials may be defined by presence of several relative minor non-plastic elements, such as a few screws or a spring, within the holder—which otherwise is formed from plastic.

In preferred embodiments—the syringe holder may be arranged to releasably couple to a relative rear portion of a syringe (see dashed arrow in FIG. 9B) adjacent a rear portion of the syringe's barrel—leaving a forward portion of the syringe (see full arrow in FIG. 9B) substantially exposed.

Such arrangement of leaving a substantial portion of the syringe exposed may be useful throughout various procedures within the apparatus, such as when navigating the syringe into narrow or small areas (such as towards and/or into the metering station, septum, cap—etc.).

In at least certain embodiments, leaving a substantial portion of the syringe exposed may be useful also in releasing the syringe from its grip within the syringe holder. For example, in embodiments where the syringe may be inserted into pig holder 2030, the substantial portion of the exposed syringe able to enter the pig holder—provides sufficient support for urging the syringe out of its grip within the syringe holder (see transition from FIG. 14B to 14C where movement of the pig holder to the left is seen releasing the syringe from its grip within the syringe holder).

During operation of the apparatus, sway member 1062 may be urged to move in relation to the bracket 1061 and snap 1063, as illustrated by the vertical dashed arrow in FIG. 9A. This may in turn result in ingress (or egress) of liquids into (or out of) the syringe—by moving the plunger in relation to the syringe's barrel, which remains fixed in place within holder 1060 by the bracket 1061 and snap 1063.

Figure 11:
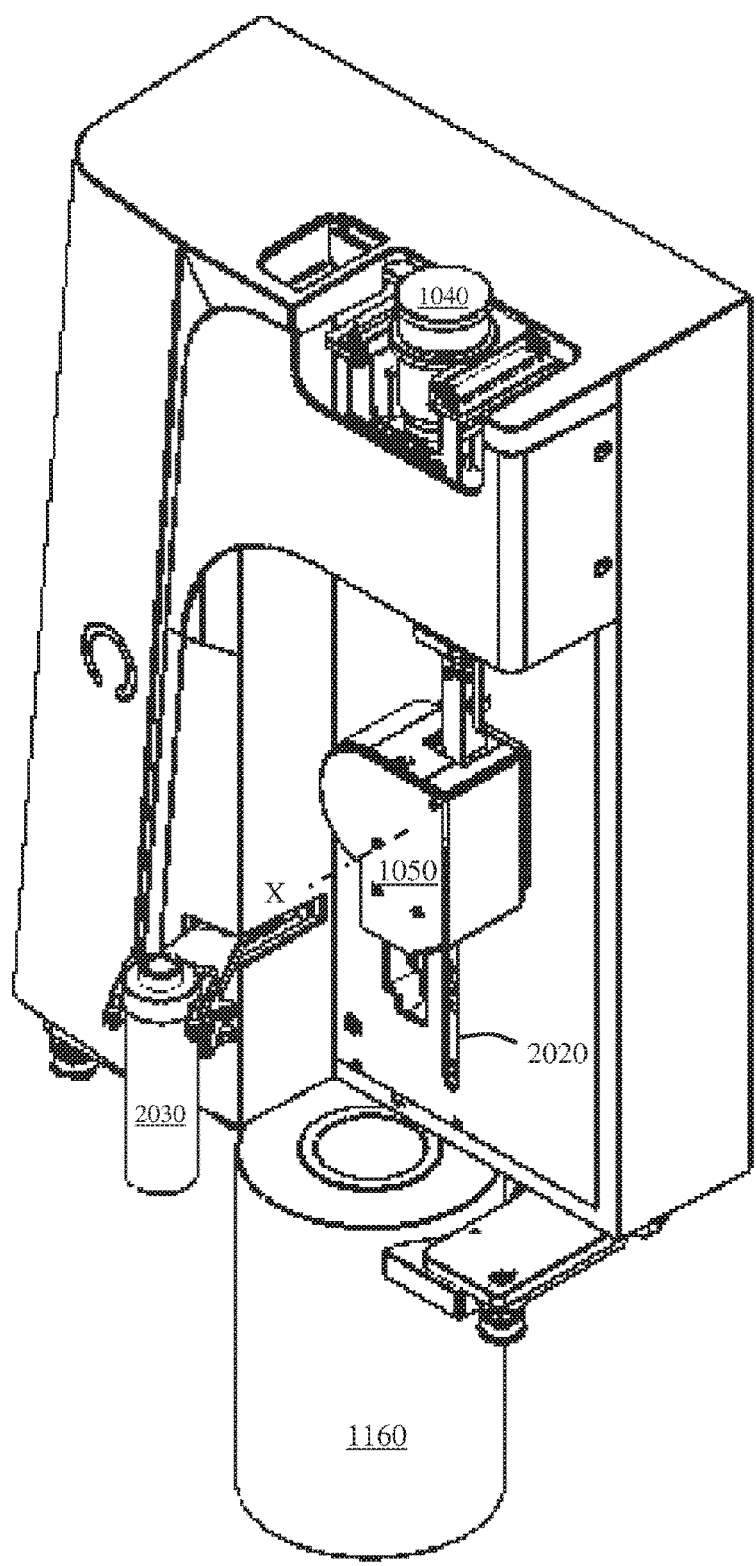

From the loading state seen in FIG. 9A, the syringe holder 1060 may be urged away from cap holder 1205 in this example in an upward direction in order to remove cap 1201 from the syringe and by that expose the needle of the syringe. Attention is additionally drawn to FIGS. 10 and 11 illustrating transitions that the syringe may undergo from the state of the apparatus seen in FIG. 9B. FIG. 10 may represent an intermediate state where the syringe has been rotated about 90 degrees here counter-clockwise towards the state of the apparatus seen in FIG. 11 where the syringe is oriented facing with its needle upwards. The transition of the syringe from the position seen in FIG. 9B towards that seen in FIG. 11 may include movements of hub 1050 both along slide 2020 and/or about axis X.

At the position seen in FIG. 11, the syringe may be urged upwards to penetrate a septum of a container held within a container holder 1040 that may be filled with liquid (possibly including radiant materials). Prior to penetrating the container, a calibration process such as that mentioned herein above with respect to FIGS. 5 to 7—may be performed, resulting in a "correction value" that assists in orienting a needle of a specific syringe being manipulated within the apparatus with axes of the apparatus.

Such a "correction value" detected e.g. prior to penetrating the container may be used also for correcting e.g. rotation of the syringe holder about axis X when inserting the needle of the same syringe into cap holder (or the like). The "correction value" may also be derived during other stages within the apparatus such as at or after loading a new syringe to the apparatus—wherein in such case said "correction value" may later be used e.g. for successfully penetrating with the same syringe the container.

The filling of the syringe may include urging sway member 1062 away from bracket 1061 and snap 1063 in order to activate ingress of liquid into the syringe. The amount of liquid entering the syringe may be a pre-specified amount defined by a software in communication with the apparatus that may be arranged to store and track the liquid being distributed into each syringe.

To reduce likelihood of un-intended leak of liquid out of the container, in at least certain embodiments—liquid may be stored within the container under vacuum. Thus, in at least certain embodiments, the procedure of sucking liquid out of the container may include precaution steps to maintain vacuum conditions within the container.

In a first possible precaution step, the syringe prior to entering the container may be urged to ingress a small amount of air from the ambient environment by slightly urging the syringe's plunger out of its barrel. The amount of air sucked into the syringe may preferably be equal or better smaller than the amount of liquid that is planned to be removed from the container.

Upon penetrating the container, a subsequent precaution step may include egressing the air contained in the syringe into the container. Since, the container is preferably held in the apparatus with its septum facing downwards, the air entering the container from below—rises upwards towards an upper face of the liquid stored in the container. Once this step is complete, ingress of liquid from the container into the syringed may occur—while ensuring that vacuum conditions remain in the container.

Figure 12:
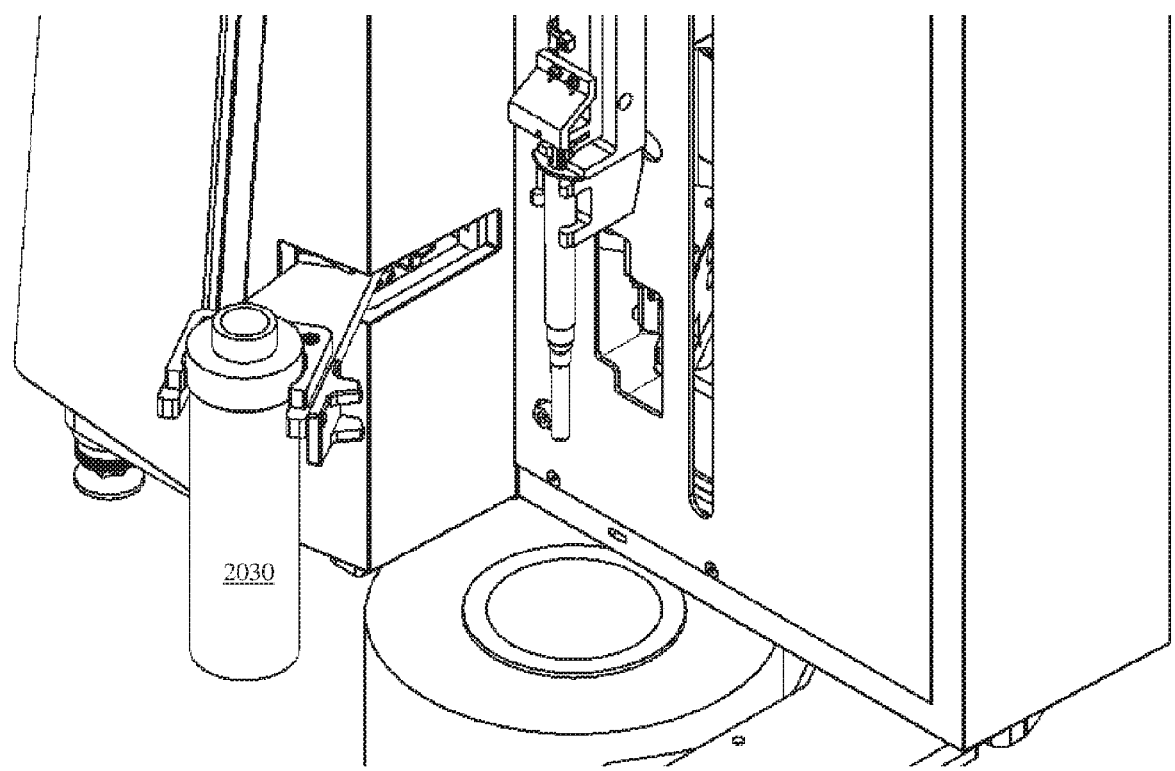

After retreating the syringe out if the container, the apparatus may urge the syringe back towards the position seen in FIG. 9B, by again urging movements of hub 1050 both along slide 2020 and/or about axis X. The needle of the syringe may then re-enter the cap as seen in FIG. 9A. From this position, the cap holder may be urged rearwardly to the right direction as indicated by the horizontal dotted arrow in FIG. 9A to snap off from the cap that remains fitted on the syringe to cover its needle as seen in FIG. 12.

Figure 13:
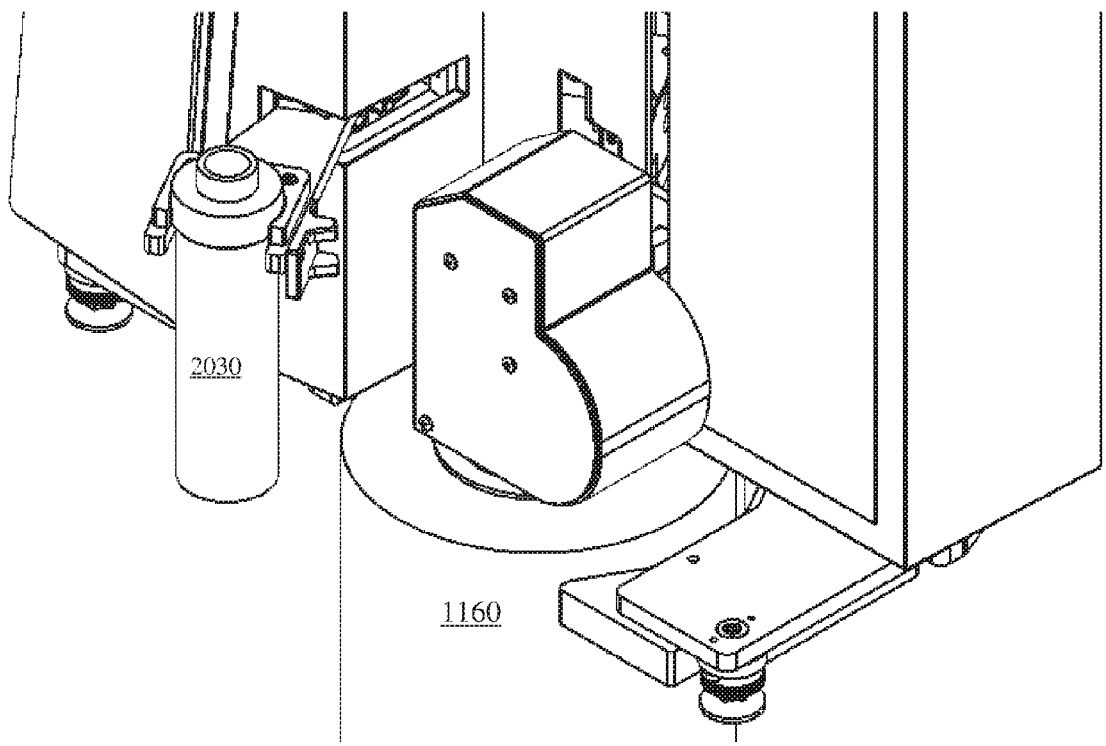

The syringe may then be urged into the metering station 1160 to verify that measured radiation is compatible with the dose of liquid just removed out of the container. If measurements determine that additional liquid should be removed from the container, the cap may be removed by snapping the cap holder back onto the cap (to the position seen in FIG. 9A) and then retreating the syringe away from the cap (as seen in FIG. 9B) to repeat the steps seen in FIGS. 10 and 11 to remove an additional dose of liquid from the container—and then repeat the steps described in FIGS. 12 and 13 to confirm that the correct dose has now been removed. It is noted that the abovementioned procedure may also be used for removing liquid from the syringe—e.g. if measurements at metering station 1160 determine that some liquid should be returned to the container.

Figure 15A:
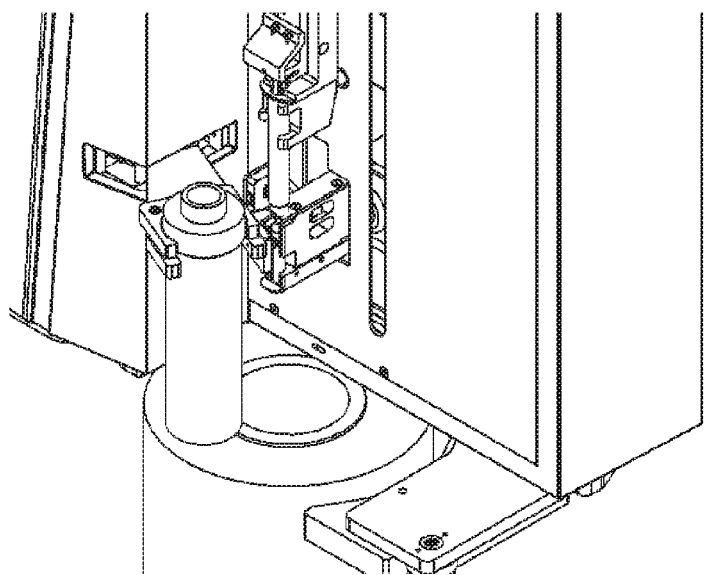
Figure 15B:
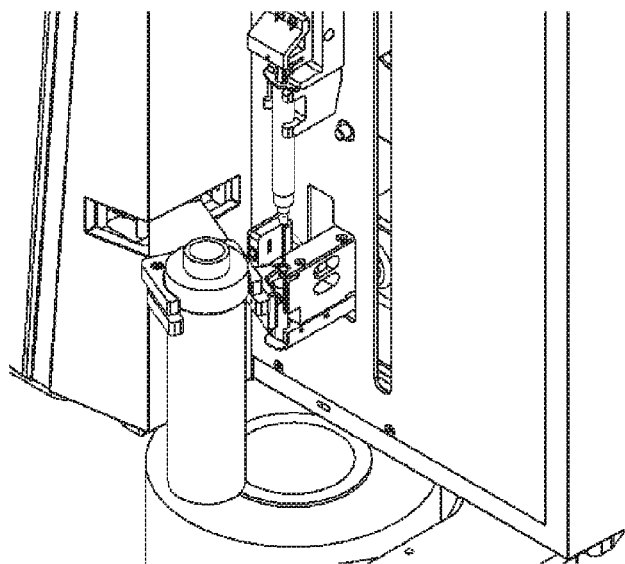

In at least certain embodiments, the procedure of snapping the cap holder back into engagement with the cap may include steps illustrated in FIGS. 15A and 15B. From the position seen in FIG. 12 where the syringe is held with the cap extending down—the pig holder 2030 may be urged to rotate (see FIG. 15A) in this example counter-clockwise to bear against the cap to support the syringe at the cap—while the cap holder re-appears from within a housing of the apparatus to snap onto and firmly grip the cap. Removal of the syringe from the cap may then be performed as illustrated in FIG. 15B by urging the syringe upwards, while the cap is gripped within the cap holder.

Figure 14A:
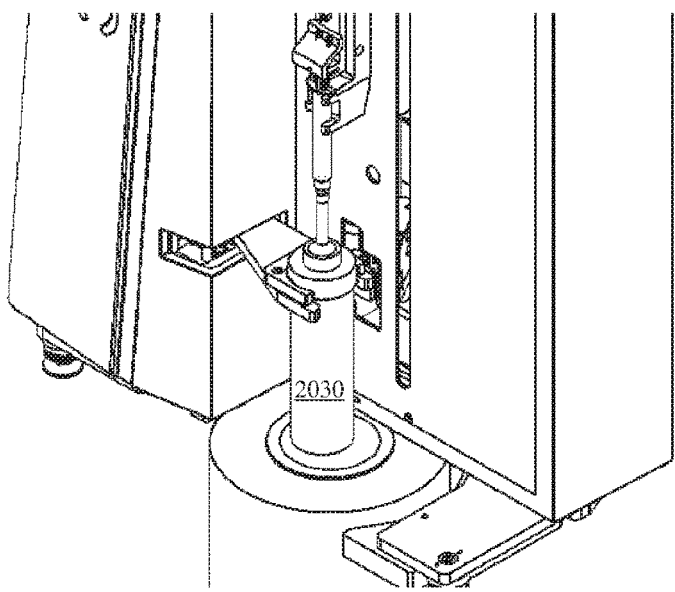
Figure 14B:
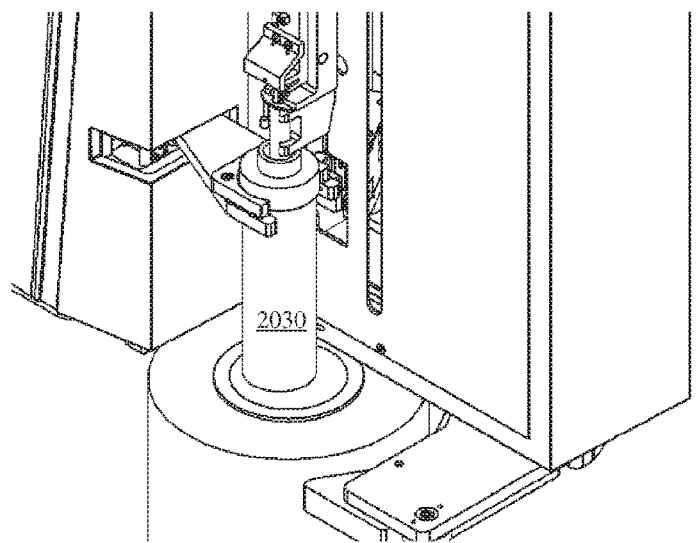
Figure 14C:
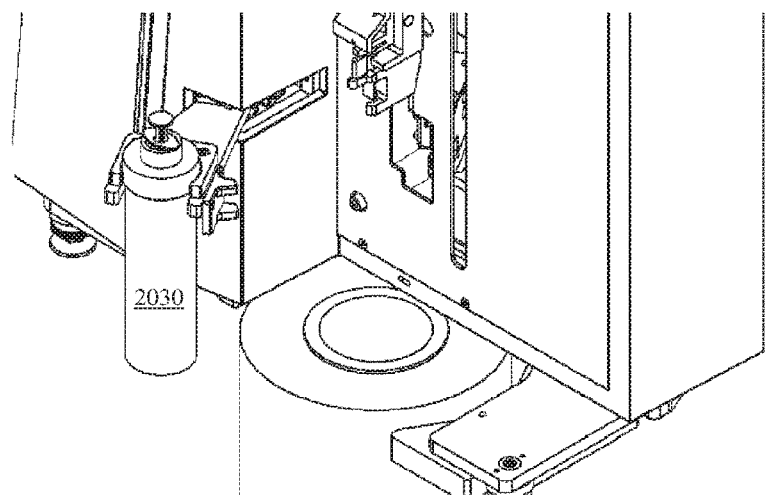

Once confirming that a correct dose is present within the syringe, from the position seen in FIG. 12—the apparatus may urge the pig holder 2030 to rotate towards a position below the syringe as seen in FIG. 14A. The syringe may then be lowered into the pig holder 2030 as illustrated in FIG. 14B—and then a terminal stage may be performed of rotating the pig holder 2030 away from the syringe holder 1060 and by that releasing the grip of the syringe holder 1060 on the syringe by snapping the syringe's barrel out of snap 1063 of the syringe holder 1060.

Figure 16:
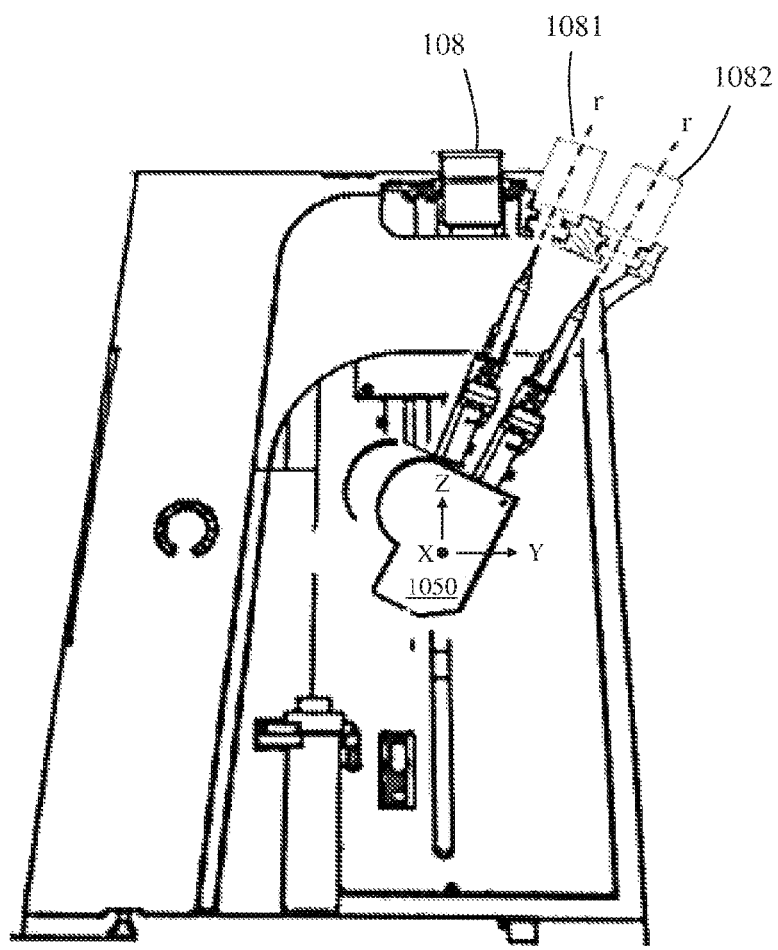
FIGS. 16, 17A and 17B illustrated various further embodiments possibly combinable with any one of the former embodiments herein of the present invention.

Attention is drawn to FIG. 16 illustrating possible presence of more than one container in at least certain apparatus embodiments. In this example, two additional containers 1081, 1082 (in some cases may be referred to as "secondary" containers) are shown in addition to container 108 (in some case may be referred to as "main" container) making a total of three such containers, however any number of additional "secondary" containers such as one (making a total of two) or more—may be possible.

In certain cases, a "secondary" container may contain fluid that is not necessarily radiant such as saline—and may be used for diluting radiant fluid within a syringe. For example, after inspection at metering station that dictates that the dose is too high—the syringe bearing such dose may be urged by the apparatus to withdraw fluid from a "secondary" container—in order (in this example) to dilute the dose of fluid within the syringe.

As illustrated, such "secondary" containers may be oriented in the apparatus along axes 'r' that extend radially away from axis X (possibly within plane Y-Z). Thus, entry of a syringe's needle into a septum of such radially oriented "secondary" container may be facilitated by combined movements, e.g. of hub 1050, both about axis X and along axis Z.

Figure 17A:
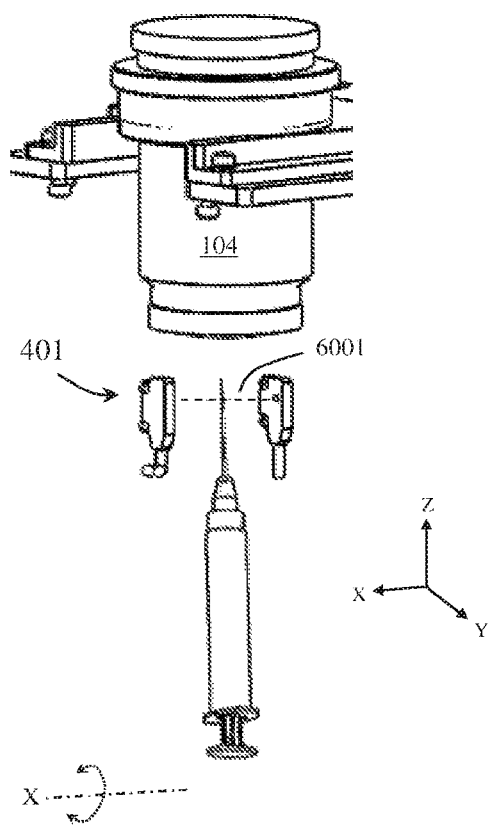
Figure 17B:
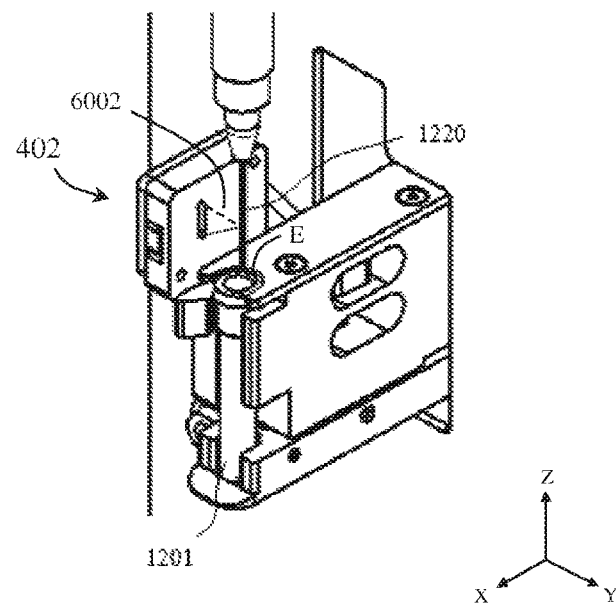

Attention is drawn to FIGS. 17A and 17B illustrating embodiments of optional first 401 and second 402 calibration apparatuses that may be comprised in at least certain apparatus embodiments. It is noted that while in certain embodiments, both calibration apparatuses 401, 402 may be deployed—in certain cases—only one of the calibration apparatuses may be used (e.g. only 401 or 402).

With attention initially drawn to FIG. 17A, calibration apparatus 401 is seen deployed at a location generally adjacent to container holder 104 and consequently container 108. Calibration apparatus 401 may include a transmitter that transmits a signal 6001 (possibly an optical signal) and receiver for receiving the signal. A syringe guided to position its needle below the container's septum, may be guided to intercept signal 6001 to ensure that the needle is correctly orientated to enter the container to draw a dose of fluid.

In an embodiment, calibration apparatus 401 and consequently signal 6001 me be arranged to detect correct placement of the needle about axis X (an axis about which hub, here not seen, may be suited to rotate a syringe). Detection of correct placement of a needle about axis X, in at least certain embodiments, may be obtained by directing signal 6001 along an axis generally parallel to axis X.

Once intercepting signal 6001—a possible "correction value" may be derived defining an 'angular correction' that rotation about axis X may take into consideration in order to suitably "aim" a needle of a given syringe within the apparatus—to successfully enter or penetrate into an aperture, entry or septum such as of the container, needle cap (or the like).

With attention additionally drawn to FIG. 17B, calibration apparatus 402 is seen fixed to a location along the cap holder generally adjacent and/or aligned to where an entry 'E' into the cap 1201 is located. Calibration apparatus 402 may include (in this optional example) a transceiver that can transmit and receive a signal 6002 (possibly an optical signal). Here, signal 6002 is schematically illustrated to include a first "dashed" path away from the transceiver and a second "dotted" path back towards the transceiver when signal 6002 is intercepted by needle 1220.

A syringe may be guided to position its needle above cap 1201, and then cap holder together with transceiver 402 may be urged to move along an axis generally parallel to axis X until a region of the needle adjacent its tip intercepts signal 6002—to thereby detect a position along axis X where the needle is generally above entry 'E' into cap 1201.

In an embodiment, calibration apparatus 402 and consequently signal 6002 may be arranged to detect correct placement of the needle along an axis generally parallel to axis X. Detection of correct placement of a needle along axis X, in at least certain embodiments, may be obtained by directing signal 6002 along an axis generally transverse and/or orthogonal to axis X.

Once intercepting signal 6002—a possible "correction value" may be derived defining an 'axial correction' that translation of the cap holder along axis X should take into consideration in order to correctly "aim" a needle of a given syringe within the apparatus—to successfully enter or penetrate into an aperture, entry or septum such as of the container, needle cap (or the like).

In embodiments including both calibration apparatus 401 and 402—final entry of a needle of a given syringe e.g. into its cap may take into consideration both the 'axial correction' and the 'angular correction' in order to substantially accurately enter into a required region—such as here the cap.

Those versed in the art will understand that modifications of various components of the apparatuses and embodiments described herein may be made without departing from the full scope and spirit of the present invention, which encompass such modifications and any and all equivalents thereof.

The invention claimed is:

1. An apparatus for filling syringes with verified doses of fluid the apparatus comprising:
   at least one container for holding fluid, and
   a syringe holder configured for releasable coupling to each syringe that is loaded to the apparatus, wherein
   the syringe holder is arranged to continuously grip a syringe loaded to the apparatus while moving the gripped syringe to draw a dose of fluid at the at least one container, wherein the syringe holder is arranged for releasing the grip from syringe when it comprises a verified dose of fluid, and wherein
   the syringe holder is arranged to urge drawing of the dose of fluid from the at least one container, by urging relative movement between a plunger and a barrel of the syringe, and wherein
   the at least one container is located generally above the syringe holder, and wherein movement of the syringe holder towards the at least one container comprises urging the syringe holder upwards.

2. The apparatus of claim 1, wherein movement of the syringe holder towards the at least one container comprises rotating the syringe holder.

3. The apparatus of claim 1 and comprising a loading position where a syringe comprising a needle attached to its tip can be loaded to the apparatus by being coupled to the syringe holder and wherein a syringe coupled to the syringe holder when in the loading position at least initially points with its needle generally downwards.

4. The apparatus of claim 3, wherein a syringe gripped by the syringe holder when at a position suitable for drawing a dose of fluid from the at least one container points with its needle generally upwards.

5. The apparatus of claim 3 and being arranged when coupling a syringe to the syringe holder to couple via a cap holder of the apparatus to a cap fitted on a needle of the syringe, and the apparatus being further arranged when moving the syringe holder away from the loading position to release the needle of the syringe from the cap that remains gripped at the cap holder.

6. The apparatus of claim 1 and comprising or being associated with a metering station for verifying doses of radiant fluid drawn out of the at least one container and comprising a pig holder for receiving a syringe filled with a dose drawn out of the at least one container, and wherein the syringe holder is substantially made from plastic materials, and the apparatus comprising a container holder formed from radiation-opaque materials for housing at least one of the containers substantially concealed therein.

7. A method for filling a syringe with a dose of fluid, comprising the steps of:
   providing an apparatus comprising at least one container for holding fluid, and a syringe holder for releasably coupling to a syringe, and
   urging the syringe holder to move towards the at least one container to draw a dose of fluid from the at least one container while continuously gripping onto the syringe until it comprises a verified dose of fluid, wherein
   the apparatus comprising a loading position where a syringe can be loaded to the apparatus by being coupled to the syringe holder, and
   coupling a syringe to the syringe holder at the loading position comprises coupling a cap fitted on a needle of the syringe to a cap holder of the apparatus, and wherein moving the syringe holder away from the loading position comprises urging the cap that remains in the cap holder to be released from its position over the needle.

8. The method of claim 7, wherein drawing the dose of fluid from the at least one container is urged via the syringe holder, by urging relative movement between a plunger and a barrel of the syringe, and wherein movement of the syringe holder towards the at least one container comprises urging the syringe holder upwards, and wherein movement of the syringe holder towards the at least one container comprises rotating the syringe holder.

9. The method of claim 8 and comprising or being associated with a metering station for verifying doses of radiant fluid drawn out of the at least one container, and wherein after verification if a change in a verified dose is required, the apparatus is adapted to urge the syringe back towards the at least one container to apply the change, where the change may be any one of: increase, decrease or dilution to be effected to the dose.

10. The method of claim 7 and comprising a step of calibrating an orientation of a syringe coupled to the syringe holder relative to another part of the apparatus, and wherein the other part is the at least one container of the apparatus.

11. The method of claim 10, wherein calibration is between orientation of a needle of a syringe coupled to the syringe holder and a septum of the at least one container adapted to be penetrated by the needle to draw fluid, and wherein the calibration step derives at least one correction value for correcting relative position or orientation between the syringe holder and other part(s) of the apparatus.

12. The method of claim 11, wherein the at least one correction value comprises rotational and/or axial correction movements to be applied to the syringe holder and/or other parts of the apparatus, and wherein correction movements assist in orienting a needle of a syringe held in the apparatus relative to an opening through which the needle is adapted to pass.

13. An apparatus for filling syringes with verified doses of radiant fluid, the apparatus comprising:
   at least one container for holding fluid, and
   a syringe holder configured for releasable coupling to each syringe that is loaded to the apparatus, wherein
   the syringe holder is arranged to continuously grip a syringe loaded to the apparatus while moving the gripped syringe to draw a dose of fluid at the at least one container, and wherein
   the apparatus comprising or being associated with a metering station for verifying doses of radiant fluid drawn out of the at least one container, and wherein after verification if a change in a verified dose is required, the apparatus is adapted to urge the syringe back towards the at least one container to apply the change, where the change may be any one of: increase, decrease or dilution to be affected to of the dose.

14. The apparatus of claim 13, wherein the syringe holder is arranged to urge drawing of the dose of fluid from the at least one container, by urging relative movement between a plunger and a barrel of the syringe.

15. The apparatus of claim 14, wherein the at least one container is located generally above the syringe holder.

16. The apparatus of claim 15, wherein movement of the syringe holder towards the at least one container comprises urging the syringe holder upwards.

17. The apparatus of claim 16 and being arranged to calibrate an orientation of a syringe coupled to the syringe holder relative to another part of the apparatus, wherein the calibration derives at least one correction value for correcting relative position or orientation between the syringe holder and other part(s) of the apparatus.

\* \* \* \* \*